United States Patent
Zang

(10) Patent No.: US 12,145,989 B2
(45) Date of Patent: *Nov. 19, 2024

(54) ANTAGONIST ANTIBODIES AGAINST HUMAN IMMUNE CHECKPOINT CEACAM1 (CD66A) AND FORMULATIONS, KITS, AND METHODS OF USE THEREOF

(71) Applicant: ALBERT EINSTEIN COLLEGE OF MEDICINE, Bronx, NY (US)

(72) Inventor: Xingxing Zang, New York, NY (US)

(73) Assignee: ALBERT EINSTEIN COLLEGE OF MEDICINE, Bronx, NY (US)

( * ) Notice: Subject to any disclaimer, the term of this patent is extended or adjusted under 35 U.S.C. 154(b) by 65 days.

This patent is subject to a terminal disclaimer.

(21) Appl. No.: 17/809,846

(22) Filed: Jun. 29, 2022

(65) Prior Publication Data

US 2023/0116037 A1 Apr. 13, 2023

Related U.S. Application Data

(63) Continuation of application No. 17/309,738, filed as application No. PCT/US2019/068176 on Dec. 20, 2019, now Pat. No. 11,377,494.

(60) Provisional application No. 62/782,785, filed on Dec. 20, 2018.

(51) Int. Cl.
*C07K 16/28* (2006.01)
*A61K 47/68* (2017.01)

(52) U.S. Cl.
CPC ...... *C07K 16/2803* (2013.01); *A61K 47/6803* (2017.08); *A61K 47/6849* (2017.08); *C07K 2317/76* (2013.01); *C07K 2317/92* (2013.01)

(58) Field of Classification Search
None
See application file for complete search history.

(56) References Cited

U.S. PATENT DOCUMENTS

| 11,377,494 B2 * | 7/2022 | Zang ................. C07K 16/2803 |
| 2004/0047858 A1 | 3/2004 | Blumberg et al. |
| 2014/0120554 A1 | 5/2014 | Markel et al. |
| 2018/0334496 A1 | 11/2018 | Perlroth et al. |

FOREIGN PATENT DOCUMENTS

| WO | 2004/29093 A2 | 4/2004 |
| WO | 2004/29094 A1 | 4/2004 |
| WO | 2013/054331 A1 | 4/2013 |
| WO | 2013/054331 A8 | 4/2013 |
| WO | 2015/166484 A1 | 11/2015 |

OTHER PUBLICATIONS

PCT Search Report and Written Opinion, PCT Appl. No. PCT/US19/68176, dated Apr. 21, 2020, 13 pages.
UniProtKB Accession No. A0A1W1YV48, Ribosome biogenesis GTPase A, Jun. 7, 2017, 5 pages.
Co-pending EP Patent Application No. 19899610.0, Partial Search Report dated Sep. 19, 2022, 17 pages.
Bonsor, et al. "Diverse oligomeric states of CEACAM IgV domains" Proceedings of the National Academy of Sciences, vol. 112, No. 44, Nov. 3, 2015, 6 pages.
Co-Pending EP Application No. 19899610.0, Communication Pursuant to Rule 114(2), Third Party Observation dated Dec. 12, 2022, 4 pages.
Extended European Search Report for European Application No. 19899610.0; Date of Mailing: Jan. 16, 2023; 15 pages.
Rudikoff, et al., "Single amino acid substitution altering antigen-binding specificity," Proceedings of the National Academy of Sciences, vol. 79, 1 March, pp. 1979-1983.

* cited by examiner

*Primary Examiner* — Phuong Huynh
(74) *Attorney, Agent, or Firm* — Perkins Coie LLP

(57) ABSTRACT

Provided are isolated antibodies and antigen-binding fragments thereof that specifically bind CEACAM1, including the IgV domain of CEACAM1, as well as pharmaceutical formulations, kits, and methods of use thereof.

9 Claims, 7 Drawing Sheets

Specification includes a Sequence Listing.

| Clone | $K_{assoc}(Ms)^{-1}$ | $K_{dissoc}(s)^{-1}$ | $K_D$ (nM) |
|---|---|---|---|
| 38B5 | 8.18E+05 | 4.82E-04 | 0.589 |
| 9B4 | 1.54E+05 | 4.84E-04 | 3.14 |
| 24E5 | 1.51E+05 | 7.06E-04 | 4.69 |
| 25C8 | 4.96E+04 | 1.93E-04 | 3.88 |
| 26H6 | 3.26E+04 | 4.55E-04 | 14.0 |
| 29F5 | 6.65E+04 | 3.96E-04 | 5.96 |
| 31A9 | 1.65E+04 | 9.44E-05 | 5.72 |
| 32B3 | 2.30E+04 | 1.37E-04 | 5.95 |
| 23A8 | 2.19E+04 | 2.04E-03 | 93.1 |
| 36B11 | 7.61E+04 | 1.08E-04 | 1.42 |

Fig. 3

ANTAGONIST ANTIBODIES AGAINST HUMAN IMMUNE CHECKPOINT CEACAM1 (CD66A) AND FORMULATIONS, KITS, AND METHODS OF USE THEREOF

PRIORITY CLAIM

This application is a continuation of U.S. patent application Ser. No. 17/309,738, filed Jun. 16, 2021, now, U.S. Pat. No. 11,377,494, which is a 371 of International Patent No. PCT/US2019/068176, filed Dec. 20, 2019, which claims priority to U.S. Provisional Appl. No. 62/782,785, filed on Dec. 20, 2018, the disclosure of which is hereby incorporated by reference herein in its entirety.

The instant application contains a Sequence Listing which has been submitted electronically in ASCII format and is hereby incorporated by reference in its entirety. Said ASCII copy, created on Jun. 15, 2021, is named SequenceListing.txt and is 22,373 bytes in size.

BACKGROUND

Carcinoembryonic-antigen-related cell-adhesion molecule 1 (CEACAM11), also known as BGP, C-CAM, and CD66a, is a type I transmembrane protein. CEACAM1 has an N-terminal variable immunoglobulin domain (IgV), up to three constant C2-like immunoglobulin (IgC) domains, a transmembrane region, and a cytoplasmic tail with an immunoreceptor tyrosine-based inhibition motif (ITIM). The human CEACAM1 gene can produce 12 different alternatively spliced isoforms, and all 12 isoforms contain the same N-terminal IgV domain. The extracellular IgV domain of CEACAM1 is essential to its function, as it is required for homophilic or heterophilic interactions. CEACAM1 can express on T cells and NK cells. The IgV domains of two CEACAM1 proteins interact to induce negative signaling via ITIM motifs in T cell and NK cells.

SUMMARY

Provided herein in certain embodiments are isolated antibodies or antigen-binding fragments thereof that specifically bind CEACAM1, including human CEACAM1 comprising the amino acid sequence set forth in SEQ ID NO:31.

In certain embodiments, the antibodies or antigen-binding fragments thereof provided herein bind CEACAM1 with a binding affinity of at least 1.5 nM $K_D$, 1.0 nM $K_D$, 0.5 nM $K_D$, or 0.25 nM $K_D$. In certain embodiments, the antibodies or antigen-binding fragments thereof bind the IgV domain of human CEACAM1.

In certain embodiments, the antibodies or antigen-binding fragments thereof provided herein antagonize CEACAM1 activity. In certain of these embodiments, the antibodies or antigen-binding fragments thereof bind to the IgV domain of CEACAM1 and inhibit the interaction of the bound IgV domain with the IgV domain of other CEACAM1 proteins. In certain embodiments, the antibodies or antigen-binding fragments thereof inhibit CEACAM1-modulated production of one or more cytokines by a human mature dendritic cell or human T cell. In certain of these embodiments, the one or more cytokines may include IFN-7, IL-2, IL-17A, IL-17F, IL-6, IL-9, and/or TNF-α.

In certain embodiments, the antibodies or antigen-binding fragments thereof provided herein comprise:

(a) a heavy chain variable region comprising one or more of

GYIFRNYGMN, (SEQ ID NO: 13)

WINTYTGEPTYADDFKG, (SEQ ID NO: 14)
and

RGWLLTGGAMDY; (SEQ ID NO: 15)

(b) a light chain variable region comprising one or more of:

RASQDIGSSLN, (SEQ ID NO: 16)

ATSSLDS, (SEQ ID NO: 17)
and

LQYVSSPWT; (SEQ ID NO: 18)

(c) a heavy chain variable region comprising one or more of

GYIFRNYGMN, (SEQ ID NO: 19)

WINTYTGEPTYADDFKG, (SEQ ID NO: 20)
and

DCGTSHYYAMDY; (SEQ ID NO: 21)

(d) a light chain variable region comprising one or more of:

RASQDISNYLN, (SEQ ID NO: 22)

YTSRLHS, (SEQ ID NO: 23)
and

QQGNTFPLT; (SEQ ID NO: 24)

(e) a heavy chain variable region comprising one or more of

GYAFTIYLIE, (SEQ ID NO: 25)

VINPGSGGTNYNEKFKG, (SEQ ID NO: 26)
and

SYYYGSFAMDY; (SEQ ID NO: 27)

(f) a light chain variable region comprising one or more of:

RASQDIGNYLN, (SEQ ID NO: 28)

YTSRLHS, and (SEQ ID NO: 29)

QQGNTLRT. (SEQ ID NO: 30)

In certain embodiments, the antibodies or antigen-binding fragments thereof provided herein comprise:

(a) a heavy chain variable region comprising one or more of

GYIFRNYGMN, (SEQ ID NO: 13)

WINTYTGEPTYADDFKG, and (SEQ ID NO: 14)

RGWLLTGGAMDY; (SEQ ID NO: 15)

and a light chain variable region comprising one or more of:

RASQDIGSSLN, (SEQ ID NO: 16)

ATSSLDS, and (SEQ ID NO: 17)

LQYVSSPWT; (SEQ ID NO: 18)

(b) a heavy chain variable region comprising one or more of

GYIFRNYGMN, (SEQ ID NO: 19)

WINTYTGEPTYADDFKG, and (SEQ ID NO: 20)

DCGTSHYYAMDY; (SEQ ID NO: 21)

and a light chain variable region comprising one or more of:

RASQDISNYLN, (SEQ ID NO: 22)

YTSRLHS, and (SEQ ID NO: 23)

QQGNTFPLT; (SEQ ID NO: 24)

(c) a heavy chain variable region comprising one or more of

GYAFTIYLIE, (SEQ ID NO: 25)

VINPGSGGTNYNEKFKG, and (SEQ ID NO: 26)

SYYYGSFAMDY; (SEQ ID NO: 27)

and a light chain variable region comprising one or more of:

RASQDIGNYLN, (SEQ ID NO: 28)

YTSRLHS, and (SEQ ID NO: 29)

QQGNTLRT. (SEQ ID NO: 30)

In certain embodiments, the antibodies or antigen-binding fragments thereof provided herein comprise:
 (a) a heavy chain variable region comprising SEQ ID NO:2;
 (b) a light chain variable region comprising SEQ ID NO:4;
 (c) a heavy chain variable region comprising SEQ ID NO:6;
 (d) a light chain variable region comprising SEQ ID NO: 8;
 (e) a heavy chain variable region comprising SEQ ID NO: 10; or
 (f) a light chain variable region comprising SEQ ID NO:12.

In certain embodiments, the antibodies or antigen-binding fragments thereof provided herein comprise:
 (a) a heavy chain variable region comprising SEQ ID NO:2 and a light chain variable region comprising SEQ ID NO:4;
 (b) a heavy chain variable region comprising SEQ ID NO:6 and a light chain variable region comprising SEQ ID NO:8; or
 (c) a heavy chain variable region comprising SEQ ID NO:10 and a light chain variable region comprising SEQ ID NO:12.

In certain embodiments, the antibodies or antigen-binding fragments thereof provided herein specifically bind all or part of the same CEACAM1 epitope as, and/or cross-compete for CEACAM1 binding with, an antibody or antigen-binding fragment thereof specifically listed above, i.e., an antibody or fragment thereof comprising a heavy chain variable region comprising SEQ ID NOs:13-15, SEQ ID NOs:19-21, SEQ ID NO:25-27, SEQ ID NO:2, SEQ ID NO:6, or SEQ ID NO:10 and/or a light chain variable region comprising SEQ ID NOs:16-18, SEQ ID NOs:22-24, SEQ ID NOs:28-30, SEQ ID NO:4, SEQ ID NO:8, or SEQ ID NO:12.

In certain embodiments, the antibodies or antigen-binding fragments thereof provided herein are linked or conjugated to a therapeutic agent.

In certain embodiments, the antibodies or antigen-binding fragments thereof provided herein are incorporated into a fusion protein.

Provided herein in certain embodiments are nucleic acid molecules comprising a nucleic acid sequence encoding an antibody or antigen-binding fragment thereof as provided herein. In certain of these embodiments, the nucleic acid molecules comprise a nucleic acid sequence encoding:

(a) a heavy chain variable region comprising one or more of

GYIFRNYGMN, (SEQ ID NO: 13)

WINTYTGEPTYADDFKG, (SEQ ID NO: 14)
and

RGWLLTGGAMDY; (SEQ ID NO: 15)

(b) a light chain variable region comprising one or more of:

RASQDIGSSLN, (SEQ ID NO: 16)

ATSSLDS, (SEQ ID NO: 17)
and

LQYVSSPWT; (SEQ ID NO: 18)

(c) a heavy chain variable region comprising one or more of

GYIFRNYGMN, (SEQ ID NO: 19)

WINTYTGEPTYADDFKG, (SEQ ID NO: 20)
and

DCGTSHYYAMDY; (SEQ ID NO: 21)

(d) a light chain variable region comprising one or more of:

RASQDISNYLN, (SEQ ID NO: 22)

YTSRLHS, (SEQ ID NO: 23)
and

QQGNTFPLT; (SEQ ID NO: 24)

(e) a heavy chain variable region comprising one or more of

GYAFTIYLIE, (SEQ ID NO: 25)

VINPGSGGTNYNEKFKG, (SEQ ID NO: 26)
and

SYYYGSFAMDY; (SEQ ID NO: 27)

(f) a light chain variable region comprising one or more of:

RASQDIGNYLN, (SEQ ID NO: 28)

YTSRLHS, (SEQ ID NO: 29)
and

QQGNTLRT. (SEQ ID NO: 30)

In certain embodiments, the nucleic acid molecules provided herein comprise a nucleic acid sequence encoding:

(a) an antibody heavy chain variable region comprising one or more of:

GYIFRNYGMN, (SEQ ID NO: 13)

WINTYTGEPTYADDFKG, (SEQ ID NO: 14)
and

RGWLLTGGAMDY; (SEQ ID NO: 15)

an antibody heavy chain variable region comprising one or more of:

GYIFRNYGMN, (SEQ ID NO: 19)

WINTYTGEPTYADDFKG, (SEQ ID NO: 20)
and

DCGTSHYYAMDY; (SEQ ID NO: 21)

(b) an antibody heavy chain variable region comprising one or more of:

GYAFTIYLIE, (SEQ ID NO: 25)

VINPGSGGTNYNEKFKG, (SEQ ID NO: 26)
and

SYYYGSFAMDY; (SEQ ID NO: 27)

an antibody light chain variable region comprising one or more of:

RASQDIGSSLN, (SEQ ID NO: 16)

ATSSLDS, (SEQ ID NO: 17)
and

LQYVSSPWT; (SEQ ID NO: 18)

(c) an antibody light chain variable region comprising one or more of:

RASQDISNYLN, (SEQ ID NO: 22)

YTSRLHS, (SEQ ID NO: 23)
and

QQGNTFPLT; (SEQ ID NO: 24)

an antibody light chain variable region comprising one or more of:

RASQDIGNYLN, (SEQ ID NO: 28)

YTSRLHS, (SEQ ID NO: 29)
and

QQGNTLRT. (SEQ ID NO: 30)

In certain embodiments, the nucleic acid molecules provided herein comprise a nucleic acid sequence encoding:
(a) a heavy chain variable region comprising SEQ ID NO:2;
(b) a light chain variable region comprising SEQ ID NO:4;
(c) a heavy chain variable region comprising SEQ ID NO:6;
(d) a light chain variable region comprising SEQ ID NO:8;
(e) a heavy chain variable region comprising SEQ ID NO:10; or
(f) a light chain variable region comprising SEQ ID NO:12.

In certain embodiments, the nucleic acid molecules provided herein comprise a nucleic acid sequence encoding:
(a) a heavy chain variable region comprising SEQ ID NO:2 and a light chain variable region comprising SEQ ID NO:4;
(b) a heavy chain variable region comprising SEQ ID NO:6 and a light chain variable region comprising SEQ ID NO:8; or
(c) a heavy chain variable region comprising SEQ ID NO:10 and a light chain variable region comprising SEQ ID NO:12.

In certain embodiments, the nucleic acid molecules provided herein comprise a nucleic acid sequence having the sequence set forth in any of SEQ ID NOs:1, 3, 5, 7, 9, or 11. In other embodiments, the nucleic acid molecules provided herein comprise a nucleic acid sequence having the set forth in any of SEQ ID NOs:1, 3, 5, 7, 9, or 11, but with the portion encoding a leader sequence removed (e.g., a nucleic acid molecule comprising nucleotides 58-420 of SEQ ID NO:1, nucleotides 61-389 of SEQ ID NO:3, nucleotides 58-404 of SEQ ID NO:5, nucleotides 61-395 of SEQ ID NO:7, nucleotides 58-417 of SEQ ID NO:9, or nucleotides 61-392 of SEQ ID NO:11).

Provided herein in certain embodiments are vectors comprising one or more of the nucleic acid molecules provided herein. Provided herein in certain embodiments are host cells comprising one or more of the vectors provided herein. Further provided in certain embodiments are methods of culturing the host cells provided herein to produce one or more of the antibodies or antigen-binding fragments thereof provided herein.

Provided herein in certain embodiments are pharmaceutical formulations comprising an antibody or antigen-binding fragment thereof as provided herein. In certain embodiments, these pharmaceutical formulations further comprise a pharmaceutically acceptable carrier and/or excipient.

Provided herein in certain embodiments are methods of inhibiting human CEACAM1 activity comprising contacting human CEACAM1 with an antibody or antigen-binding fragment thereof as provided herein in an amount sufficient to inhibit CEACAM1 activity. In certain of these embodiments, binding of the antibody or antigen-binding fragment thereof inhibits interaction between multiple CEACAM1 proteins.

Provided herein in certain embodiments are methods of inhibiting human CEACAM1 activity in a cell comprising contacting the cell with an antibody or antigen-binding fragment thereof as provided herein. In certain of these embodiments, binding of the antibody or antigen-binding fragment thereof inhibit CEACAM1-modulated cytokine production in the cell. In certain embodiments, the cell is a human mature dendritic cell or T cell.

Provided herein in certain embodiments are methods of inhibiting CEACAM1 activity in a subject comprising administering to the subject an antibody or antigen-binding fragment thereof or pharmaceutical formulation as provided herein in an amount sufficient to inhibit CEACAM1 activity. In certain of these embodiments, administration of the antibody or antigen-binding fragment thereof inhibits CEACAM1-modulated cytokine production in said subject.

Provided herein in certain embodiments are methods of treating a condition associated with CEACAM1 expression or activity in a subject in need thereof comprising administering to the subject a therapeutically effective amount of an antibody or antigen-binding fragment thereof or pharmaceutical formulation as provided herein. In certain embodiments, the condition associated with CEACAM1 expression or activity is cancer.

Provided herein in certain embodiments are methods of treating cancer in a subject in need thereof comprising administering to the subject a therapeutically effective amount of an antibody or antigen-binding fragment thereof or pharmaceutical formulation as provided herein.

Provided herein in certain embodiments are methods of inhibiting CEACAM1-mediated T cell suppression in a subject in need thereof comprising administering to the subject a therapeutically effective amount of an antibody or antigen-binding fragment thereof or pharmaceutical formulation as provided herein.

Provided herein in certain embodiments are methods of inhibiting the interaction of IgV domains from multiple CEACAM1 proteins comprising contacting the multiple CEACAM1 proteins with an antibody or antigen-binding fragment thereof as provided herein.

Provided herein in certain embodiments are methods of detecting CEACAM1 in a cell comprising contacting the cell with an antibody or antigen-binding fragment thereof as provided herein linked or conjugated to a detectable marker, then determining whether the antibody or antigen-binding fragment binds the cell by detecting the marker.

Provided herein in certain embodiments are methods of detecting a CEACAM1-positive cell in a subject comprising administering to said subject an antibody or antigen-binding fragment thereof as provided herein linked or conjugated to a detectable marker, then detecting the marker in the subject.

Provided herein in certain embodiments are methods of detecting CEACAM1 in a biological sample comprising contacting said sample with an antibody or antigen-binding fragment thereof as provided herein linked or conjugated to a detectable marker, then detecting the marker.

Provided herein in certain embodiments are kits comprising an antibody or antigen-binding fragment thereof as provided herein and, optionally, instructions for use. In certain embodiments, the kit is for use in inhibiting CEACAM1 activity in a cell or subject, detecting CEACAM1 in a cell, subject, or biological sample, treating a condition associated with CEACAM1 activity or expression, including cancer, or inhibiting CEACAM1-mediated T cell suppression in a subject in need thereof.

Provided herein in certain embodiments is the use of an antibody or antigen-binding fragment thereof as provided herein for the manufacture of a medicament for inhibiting human CEACAM1 activity, treating a condition associated with CEACAM1 activity or expression, including cancer, or inhibiting CEACAM1-mediated T cell suppression in a subject in need thereof.

BRIEF DESCRIPTION OF THE DRAWINGS

Those of skill in the art will understand that the drawings, described below, are for illustrative purposes only. The drawings are not intended to limit the scope of the present teachings in any way.

FIG. 3. Kinetic parameters of 10 mAbs determined by Surface Plasmon Resonance.

DETAILED DESCRIPTION OF THE INVENTION

Figure 1A:
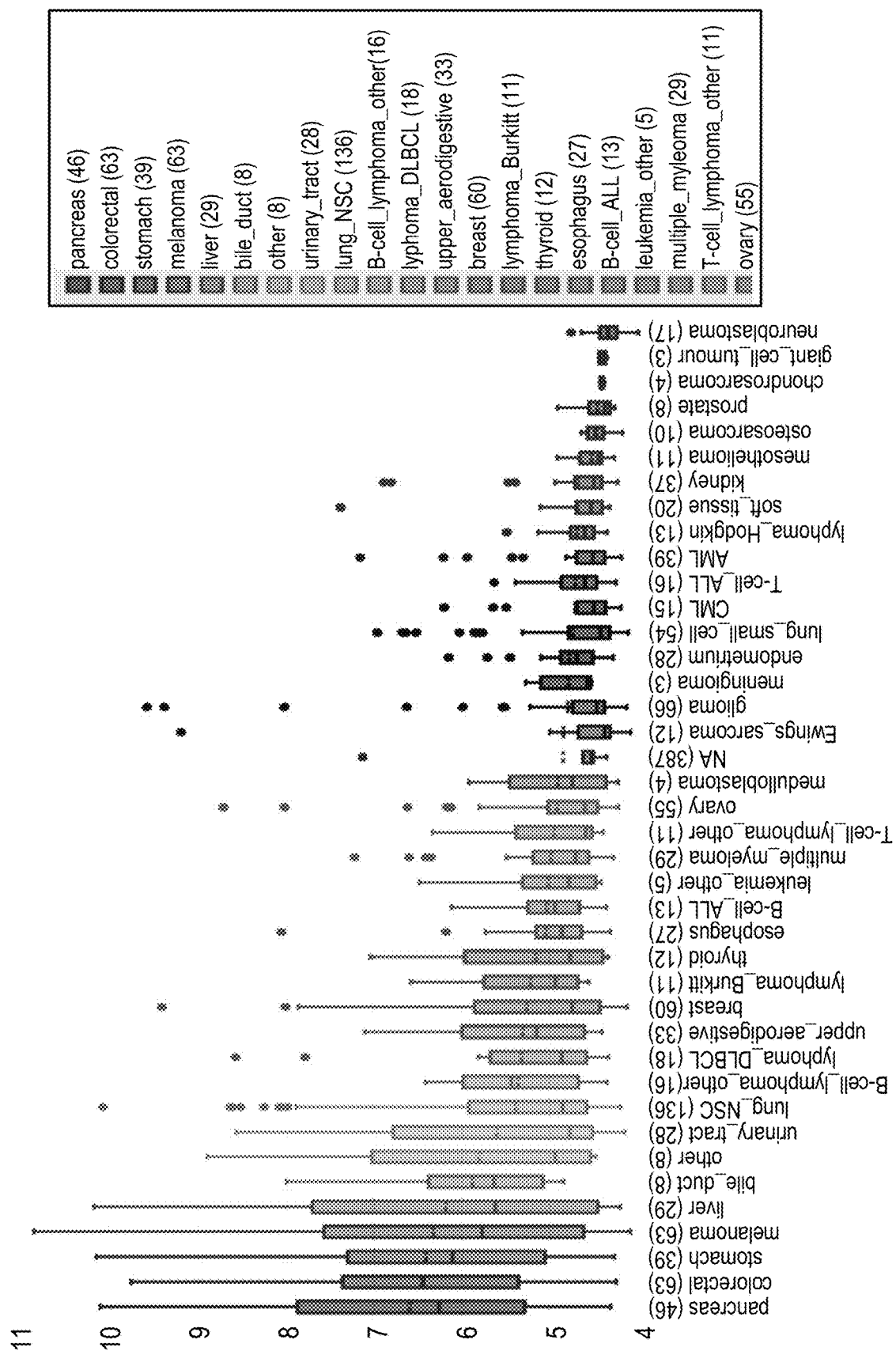
FIGS. 1A-1B. CEACAM1 is widely expressed in many human cancer lines demonstrated by Microarray (A) and RNA-sequencing (B).

As disclosed herein, novel monoclonal CEACAM1 antibodies have been identified that specifically bind the IgV domain of human CEACAM1. Three of these antibodies were shown to recognize endogenous CEACAM1 expressed on human T cells or human dendritic cells, and all three were further found to antagonize CEACAM1 function as evidenced by their ability to significantly increase cytokine production in a mixed lymphocyte reaction.

Accordingly, the present application provides antibodies and antigen-binding fragments thereof that specifically bind CEACAM1, as well as formulations and kits comprising these antibodies and antigen-binding fragments thereof. Also provided herein are methods of using the disclosed antibodies and antigen-binding fragments thereof, formulations, and kits to inhibit CEACAM1 activity in a cell or a subject, to treat a condition associated with CEACAM1 activity or expression, to inhibit CEACAM1-mediated T cell suppression, and to detect CEACAM1 in a cell, subject, or biological sample.

Definitions

The term "antibody" as used herein refers to an intact immunoglobulin molecule, i.e., an immunoglobulin molecule with two heavy chains and two light chains and complete Fc and Fv regions. The antibody may belong to any immunoglobulin class, e.g., IgA, IgD, IgG1, IgG2, IgG3, IgM, or the like, and may be a natural antibody, synthetic antibody, monoclonal antibody, polyclonal antibody, chimeric antibody, humanized antibody, multi-specific antibody, bispecific antibody, dual-specific antibody, or anti-idiotypic antibody. The term "antigen-binding fragment thereof" as used herein with regard to an antibody refers to any immunologically active portion of an antibody, i.e., any portion of an antibody that retains the ability to bind an antigen bound by the intact antibody, as measured by the ability of the fragment to compete with the intact antibody for antigen binding. Antigen-binding fragments include, but are not limited to, a single domain antibody (sdAb) (i.e., nanobody), an Fv, a disulfide-linked Fv, a single-chain Fv (scFv), a diabody, an Fd, a Fab, a Fab', or a F(ab')$_2$, and may be prepared, for example, recombinantly or by enzymatic or chemical cleavage of an intact antibody (see, e.g., Fundamental Immunology, Ch. 7, Paul, W., ed., 2nd ed. Raven Press, N.Y. (1989), hereby incorporated by reference in its entirety).

The term "monoclonal antibody" as used herein refers to an antibody member of a population of substantially homogeneous antibodies that recognize the same antigen. The individual antibodies comprising the population of monoclonal antibodies are identical except for possible mutations, e.g., naturally occurring mutations, that may be present in minor amounts. A "polyclonal" antibody as used herein refers to an antibody member of a population of non-homogenous antibodies that recognize different epitopes.

The term "isolated" as used herein with regard to an antibody or antigen-binding fragment thereof means that the antibody or antigen-binding fragment thereof, by virtue of its origin or source of derivation, has at least one of the following characteristics: (1) not associated with naturally associated components that accompany it in its native state, (2) free of other proteins from the same species, (3) expressed by a cell from a different species, and/or (4) does not occur in nature absent the hand of man.

A "pharmaceutically acceptable carrier" as used herein refers to an excipient, diluent, preservative, solubilizer, emulsifier, adjuvant, and/or vehicle with which the present antibody or fragment is administered. Such carriers may be sterile liquids, such as water and oils, including those of petroleum, animal, vegetable or synthetic origin, such as peanut oil, soybean oil, mineral oil, sesame oil and the like, polyethylene glycols, glycerine, propylene glycol or other synthetic solvents. Antibacterial agents such as benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose may also be a carrier. Methods for producing compositions in combination with carriers are known to those of skill in the art. In some embodiments, the language "pharmaceutically acceptable carrier" is intended to include any and all solvents, dispersion media, coatings, isotonic and absorption delaying agents, and the like, compatible with pharmaceutical administration. The use of such media and agents is well known in the art. See, e.g., Remington, The Science and Practice of Pharmacy. 22nd edition, Pharmaceutical Press (2012). Except insofar as any conventional media or agent is incompatible with the active compound, such use in the compositions is contemplated.

The terms "treat," "treating," and "treatment" as used herein with regard to a condition include eliminating condition or one or more symptoms associated with the condition, reducing the severity of the condition or one or more symptoms of the condition, preventing or slowing the onset of the condition or one or more symptoms associated with the condition, preventing, slowing, or reducing the likelihood of occurrence or recurrence of the condition or one or more symptoms associated with the condition, or some combination thereof. For example, "treatment" of a solid cancer may refer to partial or total inhibition of tumor growth, reduction of tumor size, complete or partial tumor eradication, reduction or prevention of malignant growth, partial or total eradication of cancer cells, or some combination thereof. In certain embodiments, a subject is "treated" if, after receiving a therapeutic amount of an antibody provided herein or a formulation thereof, the subject shows observable and/or measurable reduction in or absence of one or more symptoms of the particular disease. Reduction of the signs or symptoms of a disease may also be felt by the subject. A subject is also considered treated if the subject experiences stable disease. Parameters for assessing successful treatment are readily measurable by routine procedures familiar to a physician of appropriate skill in the art.

As used herein, "preventative" treatment refers to preventing or slowing the onset of the condition or one or more symptoms associated with the condition, preventing, slowing, or reducing the likelihood of occurrence or recurrence of the condition or one or more symptoms associated with the condition, or some combination thereof, while "curative" treatment refers to eliminating condition or one or more symptoms associated with the condition, reducing the severity of the condition or one or more symptoms of the condition, or some combination thereof.

A "subject" as used herein refers to any animal, a non-human mammal, or a human. "Animal" in this context may include a pet, farm animal, economic animal, sport animal, or experimental animal, including for example a cat, dog, horse, cow, ox, pig, donkey, sheep, lamb, goat, mouse, rabbit, chicken, duck, goose, or primate, including a monkey or chimpanzee. The terms "patient" and "subject" are used interchangeably herein.

A "subject in need thereof" as used herein with regard to treatment of a condition refers to a subject who has been diagnosed with, is suspected of having, and/or exhibits one or more symptoms associated with the condition.

"$K_D$" as used herein refers to the dissociation constant of an antibody-antigen interaction.

The term "specific binding" or "specifically binds" as used herein with regard to an antibody or antigen-binding fragment thereof means that the antibody or antigen-binding fragment thereof reacts or associates more frequently, more rapidly, with greater duration, and/or with greater affinity with a particular antigen or epitope thereof than it does with alternative antigens or epitopes. For example, an antibody or antigen-binding fragment thereof that specifically binds human CEACAM1 IgV domain binds this domain or an epitope therein with greater affinity, with greater avidity, more readily, and/or with greater duration than it binds to other CEACAM1 domain or epitopes or to non-CEACAM1 domains or epitopes. Specifically binding does not preclude all binding to a second antigen or epitope, but in certain embodiments an antibody or antigen-binding fragment thereof that specifically binds an antigen or epitope may exclusively bind that antigen or epitope.

The term "compete" as used herein with regard to a first antibody or antigen-binding fragment thereof and a second antibody or antigen-binding fragment thereof means that the first antibody or antigen-binding fragment thereof binds to an antigen or epitope in a manner sufficiently similar to the binding of the second antibody or antigen-binding fragment thereof that binding of the first antibody or antigen-binding fragment thereof to the antigen or epitope detectably decreases binding of the second antibody or antigen-binding fragment thereof to the antigen or epitope. In certain embodiments, the converse is also true, i.e., binding of the second antibody or antigen-binding fragment thereof to the antigen or epitope detectably decreases binding of the first antibody or antigen-binding fragment thereof to the antigen or epitope, and in these embodiments the first and second antibodies or antigen-binding fragments thereof are said to "cross-compete." Regardless of the mechanism by which competition or cross-competition occurs (e.g., steric hindrance, conformational change, or binding to a common epitope, or portion thereof), the skilled artisan would appreciate, based upon the teachings provided herein, that such competing and/or cross-competing antibodies are encompassed and can be useful for the methods disclosed herein.

The "variable region" or "variable domain" of an antibody refers to the amino-terminal domains of the heavy or light chain of the antibody. The variable domain of the heavy chain may be referred to as "VH." The variable domain of the light chain may be referred to as "VL." These domains are generally the most variable parts of an antibody and contain the antigen-binding sites. The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions (HVRs) or complementarity-determining regions (CDRs) both in the light-chain and the heavy-chain variable domains. The more highly conserved portions of variable domains are called the framework regions (FR). The variable domains of native heavy and light chains each comprise four FR regions, largely adopting a beta-sheet configuration, connected by three CDRs, which form loops connecting, and in some cases forming part of, the beta-sheet structure. The CDRs in each chain are held together in close proximity by the FR regions and, with the CDRs from the other chain, contribute to the formation of the antigen-binding site of antibodies (see Kabat et al., Sequences of Proteins of Immunological Interest, Fifth Edition, National Institute of Health, Bethesda, Md. (1991)). The constant domains are not involved directly in the binding of an antibody to an antigen, but exhibit various effector functions, such as participation of the antibody in antibody-dependent cellular toxicity.

The "light chains" of antibodies (immunoglobulins) from any vertebrate species can be assigned to one of two clearly distinct types, called kappa (κ) and lambda (λ), based on the amino acid sequences of their constant domains.

"Framework" or "FR" residues are those variable domain residues other than the HVR residues as herein defined.

The term "hypervariable region" or "HVR" when used herein refers to the regions of an antibody variable domain which are hypervariable in sequence and/or form structurally defined loops. Generally, antibodies comprise six HVRs; three in the VH (H1, H2, H3) and three in the VL (L1, L2, L3). In native antibodies, H3 and L3 display the most diversity of the six HVRs, and H3 in particular is believed to play a unique role in conferring fine specificity to antibodies. See, e.g., Xu et al., Immunity 13:37-45 (2000); Johnson and Wu, in Methods in Molecular Biology 248:1-25 (Lo, ed., Human Press, Totowa, N.J., 2003). Indeed, naturally occurring camelid antibodies consisting of a heavy chain only are functional and stable in the absence of light chain (see, e.g., Hamers-Casterman 1993); Sheriff 1996). A number of HVR delineations are in use and are encompassed herein. The Kabat Complementarity Determining Regions (CDRs) are based on sequence variability and are the most commonly used (Kabat et al., Sequences of Proteins of Immunological Interest, 5th Ed. Public Health Service, National Institutes of Health, Bethesda, Md. (1991) hereby incorporated by reference in its entirety). There are CDRs 1, 2, and 3 for each of the heavy and light chains. Chothia & Lesk 1987 refers instead to the location of the structural loops. The AbM HVRs represent a compromise between the Kabat HVRs and Chothia structural loops, and are used by Oxford Molecular's AbM antibody modeling software. The "contact" HVRs are based on an analysis of the available complex crystal structures. HVRs may comprise "extended HVRs" as follows: 24-36 or 24-34 (L1), 46-56 or 50-56 (L2) and 89-97 or 89-96 (L3) in the VL and 26-35 (H1), 50-65 or 49-65 (H2) and 93-102, 94-102, or 95-102 (H3) in the VH. The variable domain residues are numbered according to Kabat et al., supra, for each of these definitions.

The term "Fc region" herein is used to define a C-terminal region of an immunoglobulin heavy chain, including native sequence Fc regions and variant Fc regions. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The C-terminal lysine of the Fc region may be removed, for example, during production or purification of the antibody, or by recombinantly engineering the nucleic acid encoding a heavy chain of the antibody. Accordingly, an intact antibody as used herein may be an antibody with or without the otherwise C-terminal lysine.

Antibodies and Antigen-Binding Fragments Thereof

Provided herein are isolated antibodies or antigen-binding fragments thereof that specifically bind CEACAM1, including CEACAM1 set forth in GenBank Accession No. AAH14473.1 and/or having the amino acid sequence set forth in SEQ ID NO:31. In certain embodiments, the antibodies or antigen-binding fragments thereof bind the IgV domain. In certain of these embodiments, the antibodies or antigen-binding fragments thereof bind an epitope located fully within the IgV domain, while in other embodiments the antibodies or antigen-binding fragments thereof bind an epitope located partially within the IgV domain, i.e., overlapping across the boundary of the IgV domain into an adjacent domain.

In certain embodiments, the antibodies or antigen-binding fragments thereof provided herein bind CEACAM1 with a $K_D$ that is less than 1 μM, less than 1 nM, or less than 10 pM. In certain embodiments, the antibodies or antigen-binding fragments provided herein bind CEACAM1 with a $K_D$ of from about $1\times10^{-9}$ M to about $1\times10^{-12}$ M. In certain embodiments, the antibodies or antigen-binding fragments thereof bind CEACAM1 with a binding affinity of at least 10 nM $K_D$, 7.5 nM $K_D$, 5 nM $K_D$, 2.5 nM $K_D$, 1.5 nM $K_D$, at least 1.0 nM $K_D$, at least 0.75 nM $K_D$, at least 0.5 nM $K_D$, at least 0.25 nM $K_D$, or at least 0.1 nM $K_D$.

In certain embodiments, the $K_D$ of a CEACAM1 antibody or antigen-binding fragment thereof may be determined by measuring binding affinity of a monofunctional Fab fragment. In certain embodiments, binding affinity may be measured by surface plasmon resonance (SPR), e.g., using a BIAcore3000™ SPR system (BIAcore Inc., Piscataway N.J.). CM5 chips can be activated with N-ethyl-N'-(3-dimethylaminopropyl)-carbodiimide hydrochloride (EDC) and N-hydroxysuccinimide (NHS) according to the supplier's instructions. The antigen can be diluted into 10 mM sodium acetate pH 4.0 and injected over the activated chip at a concentration of 0.005 mg/mL. Using variable flow time across the individual chip channels, two ranges of antigen density can be achieved: 100-200 response units (RU) for detailed kinetic studies and 500-600 RU for screening assays. Serial dilutions (0.1-10× estimated $K_D$) of purified Fab samples are injected for 1 min at 100 microliters/minute and dissociation times of up to 2 hours are allowed. The concentrations of the Fab proteins are determined by ELISA and/or SDS-PAGE electrophoresis using a Fab of known concentration (as determined by amino acid analysis) as a standard. Kinetic association rates ($k_{on}$) and dissociation rates ($k_{off}$) are obtained simultaneously by fitting the data to a 1:1 Langmuir binding model (Karlsson, R. Roos, H. Fagerstam, L. Petersson, B. (1994). Methods Enzymology 6. 99-110, the content of which is hereby incorporated in its entirety) using the BIA evaluation program. Equilibrium dissociation constant ($K_d$) values are calculated as $k_{off}/k_{on}$. This protocol is suitable for use in determining binding affinity of an antibody or fragment to any antigen. Other protocols known in the art may also be used. For example, ELISA is a protocol known in the art.

In certain embodiments, the antibodies or antigen-binding fragments thereof provided herein comprise:

(a) a heavy chain variable region comprising one or more of

GYIFRNYGMN, (SEQ ID NO: 13)

WINTYTGEPTYADDFKG, (SEQ ID NO: 14)
    and

RGWLLTGGAMDY; (SEQ ID NO: 15)

(b) a light chain variable region comprising one or more of:

RASQDIGSSLN, (SEQ ID NO: 16)

ATSSLDS, (SEQ ID NO: 17)
    and

LQYVSSPWT; (SEQ ID NO: 18)

(c) a heavy chain variable region comprising one or more of:

GYIFRNYGMN, (SEQ ID NO: 19)

WINTYTGEPTYADDFKG, and (SEQ ID NO: 20)

DCGTSHYYAMDY; (SEQ ID NO: 21)

(d) a light chain variable region comprising one or more of:

RASQDISNYLN, (SEQ ID NO: 22)

YTSRLHS, and (SEQ ID NO: 23)

QQGNTFPLT; (SEQ ID NO: 24)

(e) a heavy chain variable region comprising one or more of

GYAFTIYLIE, (SEQ ID NO: 25)

VINPGSGGTNYNEKFKG, and (SEQ ID NO: 26)

SYYYGSFAMDY; (SEQ ID NO: 27)

(f) a light chain variable region comprising one or more of:

RASQDIGNYLN, (SEQ ID NO: 28)

YTSRLHS, and (SEQ ID NO: 29)

QQGNTLRT. (SEQ ID NO: 30)

In certain embodiments, the antibodies or antigen-binding fragments thereof provided herein comprise:

(a) a heavy chain variable region comprising one or more of:

GYIFRNYGMN, (SEQ ID NO: 13)

WINTYTGEPTYADDFKG, and (SEQ ID NO: 14)

RGWLLTGGAMDY; (SEQ ID NO: 15)

and a light chain variable region comprising one or more of:

RASQDIGSSLN, (SEQ ID NO: 16)

ATSSLDS, and (SEQ ID NO: 17)

LQYVSSPWT; (SEQ ID NO: 18)

(b) a heavy chain variable region comprising one or more of

GYIFRNYGMN, (SEQ ID NO: 19)

WINTYTGEPTYADDFKG, and (SEQ ID NO: 20)

DCGTSHYYAMDY; (SEQ ID NO: 21)

and a light chain variable region comprising one or more of:

RASQDISNYLN, (SEQ ID NO: 22)

YTSRLHS, and (SEQ ID NO: 23)

QQGNTFPLT; (SEQ ID NO: 24)

(c) a heavy chain variable region comprising one or more of

GYAFTIYLIE, (SEQ ID NO: 25)

VINPGSGGTNYNEKFKG, and (SEQ ID NO: 26)

SYYYGSFAMDY; (SEQ ID NO: 27)

and a light chain variable region comprising one or more of:

RASQDIGNYLN, (SEQ ID NO: 28)

YTSRLHS, and (SEQ ID NO: 29)

QQGNTLRT. (SEQ ID NO: 30)

In certain embodiments, the antibodies or antigen-binding fragments thereof provided herein comprise:
(a) a heavy chain variable region comprising SEQ ID NO:2;
(b) a light chain variable region comprising SEQ ID NO:4;
(c) a heavy chain variable region comprising SEQ ID NO:6;

(d) a light chain variable region comprising SEQ ID NO: 8;

(e) a heavy chain variable region comprising SEQ ID NO: 10; or (f) a light chain variable region comprising SEQ ID NO: 12.

In certain embodiments, the antibodies or antigen-binding fragments thereof provided herein comprise:

(a) a heavy chain variable region comprising SEQ ID NO:2 and a light chain variable region comprising SEQ ID NO:4;

(b) a heavy chain variable region comprising SEQ ID NO:6 and a light chain variable region comprising SEQ ID NO:8; or (c) a heavy chain variable region comprising SEQ ID NO:10 and a light chain variable region comprising SEQ ID NO:12.

The antibodies provided herein include naturally-occurring antibodies, recombinant antibodies, chimeric antibodies, humanized antibodies, monoclonal antibodies, and polyclonal antibodies. The antigen-binding fragments provided herein include, but are not limited to, an sdAb, Fv, disulfide-linked Fv, scFv, diabody, Fd, Fab, Fab', or F(ab')$_2$. In certain embodiments, antigen-binding fragments thereof provided herein are at least 5, 6, 8, or 10 amino acids long. In certain of these embodiments, the fragments are at least 14, at least 20, at least 50, or at least 70, 80, 90, 100, 150, or 200 amino acids long.

In certain embodiments, an antibody or antigen-binding fragment provided herein is recombinantly produced. In certain of these embodiments, the antibody or fragment thereof is produced in a eukaryotic expression system and comprises glycosylation at a residue on the Fc portion corresponding to Asn297.

The antibodies and antigen-binding fragments thereof provided herein may be incorporated into a fusion protein. It will be readily understood by one of ordinary skill in the art that the formulations and methods provided herein may utilize such fusion proteins. For example, methods of treatment provided herein that utilize an antibody or antigen-binding fragment thereof may utilize a fusion protein comprising the antibody or antigen-binding fragment thereof.

In certain embodiments, the antibodies or antigen-binding fragments thereof provided herein inhibit CEACAM1-modulated cytokine production by a human mature dendritic cell or human T cell. In certain embodiments, the cytokine production is one or more of IFN-7, IL-2, IL-17A, IL-17F, IL-6, IL-9, or TNF-α production.

In certain embodiments, the antibodies or antigen-binding fragments thereof provided herein include all or a portion of the framework region of the light and/or heavy chain. In certain of these embodiments, the framework region is a human framework region. In other embodiments, the framework region comprises an amino acid sequence with at least 85% identity to, including at least 90%, at least 95%, at least 98%, or at least 99% identity to, a human framework region or portion thereof.

In certain embodiments, the antibodies or antigen-binding fragment thereof provided herein comprise all or a portion of a human Fc region.

In certain embodiments, the antibodies or antigen-binding fragments thereof provided herein comprise (i) a heavy chain framework region comprising the framework sequence of human germline IGHV1-2*02, IGHV1-2*03, IGHV1-2*04, IGHV1-2*05, IGHV1-2*06, IGHV1-18*04, IGHV1-69-2*01, IGHV1-46*01, IGHV7-4-1*01, IGHV7-4-1*02, IGHV7-4-1*01, IGHV7-81*01, IGHD2-8*02, IGHD3-10*01, IGHD3-10*02, IGHD3-22*01, IGHD5-18*01, IGHD5-5*01, IGHD5-12*01, IGHD5-24*01, IGHD6-25*01, IGHJ3*01, IGHJ4*01, IGHJ4*02, IGHJ4*03, IGHJ6*01, or IGHJ6*02 and/or (ii) a light chain framework region comprising the framework sequence of human germline IGKV1-17*01, IGKV1-6*01, IGKV1-6*02, IGKV1-13*02, IGKV1-27*01, IGKV1-33*01, IGKV3-7*02, IGKV4-1*01, IGKV1D-13*02, IGKV1D-33*01, IGKV3D-7*01, IGKJ1*01, IGKJ2*01, IGKJ3*01, IGKJ4*01, or IGKJ4*02.

Where an antigen-binding fragment provided herein is an scFv, it may comprise a variable domain framework sequence having a sequence identical to a human variable domain FR1, FR2, FR3, or FR4. The peptide linker in the scFv may range from about 5 to about 30 amino acids in lengths, and may comprise one or more glycine, serine, and/or threonine residues (see, e.g., Bird 1988; Huston 1988; each of which is incorporated by reference herein in its entirety).

From N-terminus to C-terminus, mature light and heavy chain variable regions comprise the regions FR1, CDR1, FR2, CDR2, FR3, CDR3 and FR4. The assignment of amino acids to each domain is in accordance with the definitions of Kabat, Sequences of Proteins of Immunological Interest (National Institutes of Health, Bethesda, Md. (1987 and 1991)); Chothia & Lesk 1987; or Chothia 1989, each of which are hereby incorporated by reference in their entirety).

In certain embodiments, the antibodies or antigen-binding fragments thereof provided herein are humanized, i.e., they are chimeric antibodies that contain minimal sequence derived from non-human immunoglobulin. In certain of these embodiments, the humanized antibody is a human immunoglobulin (recipient antibody) in which residues from an HVR or CDR of the recipient are replaced by residues from an HVR or CDR of a non-human species (donor antibody) such as mouse, rat, rabbit, or nonhuman primate having the desired specificity, affinity, and/or capacity. A humanized antibody may comprise 1, 2, 3, 4, 5, or all 6 CDRs of both the heavy and light chains of a non-human, e.g., murine, antibody. In a preferred embodiment, framework (FR) residues of a murine mAb are replaced with corresponding human immunoglobulin variable domain framework residues. These may be modified further in embodiments to further refine antibody performance. Furthermore, in a specific embodiment, humanized antibodies may comprise residues that are not found in the recipient antibody or in the donor antibody. In an embodiment, the humanized antibodies do not comprise residues that are not found in the recipient antibody or in the donor antibody. In general, a humanized antibody will comprise substantially all of at least one, and typically two, variable domains, in which all, or in embodiments substantially all, of the hypervariable loops correspond to those of a non-human immunoglobulin, and all, or in embodiments substantially all, of the FRs are those of a human immunoglobulin sequence. The humanized antibody optionally will also comprise at least a portion of an immunoglobulin constant region (Fc), typically that of a human immunoglobulin (see, e.g., Jones 1986; Riechmann 1988; Presta 1992; Vaswani & Hamilton 1998; Harris 1995; Hurle & Gross 1994; and U.S. Pat. Nos. 6,982,321 and 7,087,409, the contents of each of which are hereby incorporated by reference herein in their entirety). In one embodiment where the humanized antibodies comprise residues that are not found in the recipient antibody or in the donor antibody, the Fc regions of the antibodies are modified as described in PCT Publ. No. WO99/58572, the contents of which are hereby incorporated by reference herein in their entirety.

Techniques to humanize a monoclonal antibody are well known and are described in, for example, U.S. Pat. Nos. 4,816,567; 5,807,715; 5,866,692; 6,331,415; 5,530,101; 5,693,761; 5,693,762; 5,585,089; and 6,180,370, the contents of which are each hereby incorporated by reference herein in their entirety. A number of "humanized" antibody molecules comprising an antigen-binding site derived from a non-human immunoglobulin have been described, including antibodies having rodent or modified rodent V regions and their associated complementarity determining regions (CDRs) fused to human constant domains (see, e.g., Winter & Milstein 1991; Lobuglio 1989; Shaw 1987; and Brown 1987, the contents of which are each hereby incorporated by reference herein in their entirety). Other references describe rodent hypervariable regions or CDRs grafted into a human supporting framework region (FR) prior to fusion with an appropriate human antibody constant domain. See, e.g., Riechmann 1988; Verhoeyen 1988; Jones 1986, the content of each of which is hereby incorporated by reference in its entirety. Another reference describes rodent CDRs supported by recombinantly veneered rodent framework regions (see EP Patent Publ. No. 519596, hereby incorporated by reference herein in its entirety). These "humanized" molecules are designed to minimize unwanted immunological response toward rodent anti-human antibody molecules which limits the duration and effectiveness of therapeutic applications of those moieties in human recipients. The antibody constant region can be engineered such that it is immunologically inert (e.g., does not trigger complement lysis) (see, e.g., PCT Publ. No. WO99/58572; UK Patent Appl. No. 9809951.8). Other methods of humanizing antibodies that may also be utilized are disclosed by Daugherty 1991; U.S. Pat. Nos. 6,180,377; 6,054,297; 5,997,867; 5,866,692; 6,210,671; and 6,350,861; and PCT Publ. No. WO01/27160, each incorporated by reference herein in its entirety.

Other forms of humanized antibodies have one or more CDRs, including all six CDRs, which are altered with respect to the original antibody. Accordingly, provided herein in certain embodiments are antibodies or antigen-binding fragments thereof which are humanized antibodies in which one or more, or all, of the CDRs are altered with respect to the original antibody. In other embodiments, humanized antibodies or antigen-binding fragments thereof provided herein do not have any CDR that has been altered with respect to the original antibody.

In certain embodiments, the antibodies or antigen-binding fragments thereof provided herein can be produced recombinantly, for example expressed using a recombinant expression vector transfected into a host cell, isolated from a recombinant combinatorial human antibody library, or isolated from an animal (e.g., a mouse) that is transgenic for human immunoglobulin genes.

Depending on the amino acid sequences of the constant domains of their heavy chains, antibodies (immunoglobulins) can be assigned to different classes. The antibodies or antigen-binding fragments thereof provided herein can be, e.g., any of an IgG, IgD, IgE, IgA or IgM antibody or fragment thereof, respectively. In certain embodiments, the antibody or antigen-binding fragment is an IgG or a fragment of an IgG, and in certain embodiments the antibody or antigen-binding fragment thereof is an IgG1, IgG2, IgG2a, IgG2b, IgG3, or IgG4. In certain embodiments, the antibody or antigen-binding fragment thereof comprises sequences from a human IgG1, human IgG2, human IgG2a, human IgG2b, human IgG3, or human IgG4. A combination of any of these antibody subtypes can also be used. One consideration in selecting the type of antibody to be used is the desired serum half-life of the antibody. For example, an IgG generally has a serum half-life of 23 days, IgA 6 days, IgM 5 days, IgD 3 days, and IgE 2 days (Abbas A K, Lichtman A H, Pober J S. Cellular and Molecular Immunology, 4th edition, W.B. Saunders Co., Philadelphia, 2000, hereby incorporated by reference in its entirety).

In certain embodiments, the antibodies or antigen-binding fragments provided herein comprise one or more modifications to the variable regions disclosed herein. For example, the antibodies or antigen-binding fragments provided herein may comprise functionally equivalent variable regions and CDRs which do not significantly affect their properties, as well as variants which have enhanced or decreased activity and/or affinity. For example, the amino acid sequence may be mutated to obtain an antibody or antigen-binding fragment thereof with the desired binding affinity to human CEACAM1 IgV. Modification of polypeptides is routine practice in the art and need not be described in detail herein. Examples of modified polypeptides include polypeptides with conservative substitutions of amino acid residues, one or more deletions or additions of amino acids which do not significantly deleteriously change the functional activity, or which mature (enhance) the affinity of the polypeptide for its ligand, or use of chemical analogs.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to an epitope tag. Other insertional variants of the antibody molecule include the fusion to the N- or C-terminus of the antibody of an enzyme or a polypeptide which increases the half-life of the antibody in the blood circulation.

Substitution variants have at least one amino acid residue in the antibody molecule removed and a different residue inserted in its place. The sites of greatest interest for substitutional mutagenesis include the hypervariable regions, but framework alterations are also contemplated. Conservative substitutions are shown in Table 1 under the heading of "conservative substitutions." If such substitutions result in a change in biological activity, then more substantial changes, denominated "exemplary substitutions" in Table 1, or as further described below in reference to amino acid classes, may be introduced and the products screened.

TABLE 1

Amino Acid Substitutions

| Original Residue | Conservative Substitutions | Exemplary Substitutions |
|---|---|---|
| Ala (A) | Val | Val; Leu; Ile |
| Arg (R) | Lys | Lys; Gln; Asn |
| Asn (N) | Gln | Gln; His; Asp, Lys; Arg |
| Asp (D) | Glu | Glu; Asn |
| Cys (C) | Ser | Ser; Ala |
| Gln (Q) | Asn | Asn; Glu |
| Glu (E) | Asp | Asp; Gln |
| Gly (G) | Ala | Ala |
| His (H) | Arg | Asn; Gln; Lys; Arg |
| Ile (I) | Leu | Leu; Val; Met; Ala; Phe; Norleucine |

TABLE 1-continued

Amino Acid Substitutions

| Original Residue | Conservative Substitutions | Exemplary Substitutions |
|---|---|---|
| Leu (L) | Ile | Norleucine; Ile; Val; Met; Ala; Phe |
| Lys (K) | Arg | Arg; Gln; Asn |
| Met (M) | Leu | Leu; Phe; Ile |
| Phe (F) | Tyr | Leu; Val; Ile; Ala; Tyr |
| Pro (P) | Ala | Ala |
| Ser (S) | Thr | Thr |
| Thr (T) | Ser | Ser |
| Trp (W) | Tyr | Tyr; Phe |
| Tyr (Y) | Phe | Trp; Phe; Thr; Ser |
| Val (V) | Leu | Ile; Leu; Met; Phe; Ala; Norleucine |

Substantial modifications in the biological properties of the antibody are accomplished by selecting substitutions that differ significantly in their effect on maintaining (a) the structure of the polypeptide backbone in the area of the substitution, for example, as a β-sheet or helical conformation, (b) the charge or hydrophobicity of the molecule at the target site, or (c) the bulk of the side chain. Naturally occurring residues are divided into groups based on common side-chain properties:

(1) Non-polar: Norleucine, Met, Ala, Val, Leu, Ile;
(2) Polar without charge: Cys, Ser, Thr, Asn, Gln;
(3) Acidic (negatively charged): Asp, Glu;
(4) Basic (positively charged): Lys, Arg;
(5) Residues that influence chain orientation: Gly, Pro; and
(6) Aromatic: Trp, Tyr, Phe, His.

Non-conservative substitutions are made by exchanging a member of one of these classes for another class.

One type of substitution, for example, that may be made is to change one or more cysteines in the antibody, which may be chemically reactive, to another residue, such as, without limitation, alanine or serine. For example, there can be a substitution of a non-canonical cysteine. The substitution can be made in a CDR or framework region of a variable domain or in the constant region of an antibody. In some embodiments, the cysteine is canonical. Any cysteine residue not involved in maintaining the proper conformation of the antibody also may be substituted, generally with serine, to improve the oxidative stability of the molecule and prevent aberrant cross-linking. Conversely, cysteine bond(s) may be added to the antibody to improve its stability, particularly where the antibody is an antibody fragment such as an Fv fragment.

The antibodies or antigen-binding fragments thereof provided herein may be modified, e.g. in the variable domains of the heavy and/or light chains, e.g., to alter a binding property of the antibody or fragment. Changes in the variable region can alter binding affinity and/or specificity. In some embodiments, no more than one to five conservative amino acid substitutions are made within a CDR domain. In other embodiments, no more than one to three conservative amino acid substitutions are made within a CDR domain. For example, a mutation may be made in one or more of the CDR regions to increase or decrease the $K_D$ of the antibody or fragment thereof for human CEACAM1, to increase or decrease $k_{off}$, or to alter the binding specificity of the antibody or fragment thereof. Techniques in site-directed mutagenesis are well-known in the art.

A modification or mutation may also be made in a framework region or constant region to increase the half-life of a CEACAM1 antibody or antigen-binding fragment thereof provided herein (see, e.g., PCT Publ. No. WO00/09560). A mutation in a framework region or constant region can also be made to alter the immunogenicity of the antibody, to provide a site for covalent or non-covalent binding to another molecule, or to alter such properties as complement fixation, FcR binding and antibody-dependent cell-mediated cytotoxicity. According to the technology, a single antibody may have mutations in any one or more of the CDRs or framework regions of the variable domain or in the constant region.

In certain embodiments, an antibody or antigen-binding fragment thereof provided herein is linked or conjugated to a therapeutic agent. In certain of these embodiments, the therapeutic agent is a cytotoxic drug, a radioactive isotope, an immunomodulator, or a second antibody.

Provided herein in certain embodiments is an isolated anti-CEACAM1 antibody or antigen-binding fragment thereof that:

a) specifically binds to the IgV domain of CEACAM1, the antibody or antigen-binding fragment thereof comprising a heavy chain variable region comprising the CDR sequences set forth in SEQ ID NOs:13-15, SEQ ID NOs:19-21, or SEQ ID NOs:25-27; and/or a light chain variable region comprising the CDR sequences set forth in SEQ ID NOs:16-18, SEQ ID NOs:22-24, or SEQ ID NOs:28-30; or b) specifically binds to the same epitope on CEACAM1 as does a reference antibody or antibody fragment, or cross-competes for specific binding to CEACAM1 or the IgV domain of CEACAM1 with a reference antibody or antibody fragment, said reference antibody or antibody fragment comprising a heavy chain variable region comprising the CDR sequences set forth in SEQ ID NOs:13-15, SEQ ID NOs:19-21, or SEQ ID NOs:25-27; and/or a light chain variable region comprising the CDR sequences set forth in SEQ ID NOs:16-18, SEQ ID NOs:22-24, or SEQ ID NOs:28-30.

In certain embodiments, an antibody or antigen-binding fragment provided herein inhibits or reduces interaction between or among the IgV domains of multiple CEACAM1 proteins or inhibits or reduces CEACAM1-modulated cytokine production by a mature dendritic cell or T cell in a subject.

In certain embodiments an antibody or antigen-binding fragment thereof as provided herein comprises a heavy chain variable region comprising an amino acid sequence with at least 85% sequence identity to SEQ ID NO:2, optionally at least 90%, 95% or 99% sequence identity to SEQ ID NO:2. In certain of these embodiments, antibody or antigen-binding fragment thereof comprises a heavy chain variable region comprising the amino acid sequence set forth in SEQ ID NO:2.

In certain embodiments an antibody or antigen-binding fragment thereof as provided herein comprises a heavy chain variable region comprising an amino acid sequence with at least 85% sequence identity to SEQ ID NO:6, optionally at least 90%, 95% or 99% sequence identity to SEQ ID NO:6. In certain of these embodiments, antibody or antigen-binding fragment thereof comprises a heavy chain variable region comprising the amino acid sequence set forth in SEQ ID NO:6.

In certain embodiments an antibody or antigen-binding fragment thereof as provided herein comprises a heavy chain variable region comprising an amino acid sequence with at least 85% sequence identity to SEQ ID NO:10, optionally at least 90%, 95% or 99% sequence identity to SEQ ID NO:10.

In certain of these embodiments, antibody or antigen-binding fragment thereof comprises a heavy chain variable region comprising the amino acid sequence set forth in SEQ ID NO:10.

In certain embodiments an antibody or antigen-binding fragment thereof as provided herein comprises a light chain variable region comprising an amino acid sequence with at least 85% sequence identity to SEQ ID NO:4, optionally at least 90%, 95% or 99% sequence identity to SEQ ID NO:4. In certain of these embodiments, antibody or antigen-binding fragment thereof comprises a light chain variable region comprising the amino acid sequence set forth in SEQ ID NO:4.

In certain embodiments an antibody or antigen-binding fragment thereof as provided herein comprises a light chain variable region comprising an amino acid sequence with at least 85% sequence identity to SEQ ID NO:8, optionally at least 90%, 95% or 99% sequence identity to SEQ ID NO:8. In certain of these embodiments, antibody or antigen-binding fragment thereof comprises a light chain variable region comprising the amino acid sequence set forth in SEQ ID NO:8.

In certain embodiments an antibody or antigen-binding fragment thereof as provided herein comprises a light chain variable region comprising an amino acid sequence with at least 85% sequence identity to SEQ ID NO:12, optionally at least 90%, 95% or 99% sequence identity to SEQ ID NO:12. In certain of these embodiments, antibody or antigen-binding fragment thereof comprises a light chain variable region comprising the amino acid sequence set forth in SEQ ID NO:12.

The term "Fc domain" herein is used to define a C-terminal region of an immunoglobulin heavy chain, including native sequence Fc regions and variant Fc regions. Although the boundaries of the Fc domain of an immunoglobulin heavy chain might vary, the human IgG heavy chain Fc domain is usually defined to stretch from an amino acid residue at position Cys226, or from Pro230, to the carboxyl-terminus thereof. The C-terminal lysine of the Fc domain may be removed, for example, by recombinantly engineering the nucleic acid encoding it. In embodiments, the antibody comprises an Fc domain. In an embodiment, the Fc domain has the same sequence or 99% or greater sequence similarity with a human IgG1 Fc domain. In an embodiment, the Fe domain has the same sequence or 99% or greater sequence similarity with a human IgG2 Fc domain. In an embodiment, the Fe domain has the same sequence or 99% or greater sequence similarity with a human IgG3 Fe domain. In an embodiment, the Fe domain has the same sequence or 99% or greater sequence similarity with a human IgG4 Fe domain. In an embodiment, the Fe domain is not mutated. In an embodiment, the Fe domain is mutated at the CH2-CH3 domain interface to increase the affinity of IgG for FcRn at acidic but not neutral pH (Dall'Acqua et al, 2006; Yeung et al, 2009). In an embodiment, the Fe domain has the same sequence as a human IgG1 Fe domain.

In certain embodiments, the antibodies or antigen-binding fragments thereof provided herein are lyophilized and/or freeze dried and are reconstituted for use.

Formulations

Provided herein in certain embodiments are formulations, including pharmaceutical formulations, comprising an antibody or antigen-binding fragment thereof as provided herein. In certain embodiments, these formulations comprise a carrier and/or an excipient.

In certain embodiments, the formulations provided herein comprise stabilizers to prevent loss of activity or structural integrity of the protein due to the effects of denaturation, oxidation, or aggregation over a period of time during storage and transportation prior to use. The formulations may comprise any combination of salts, surfactants, or pH and tonicity agents such as sugars. Where a formulation of the present technology is used for injection, it is desirable to have a pH value in an approximately neutral pH range, and it is also advantageous to minimize surfactant levels to avoid bubbles in the formulation which are detrimental for injection into subjects. In an embodiment, the formulation is in liquid form and stably supports high concentrations of bioactive antibody in solution and is suitable for inhalational or parenteral administration. In certain embodiments, the formulation is suitable for intravenous, intramuscular, intraperitoneal, intradermal and/or subcutaneous injection. In certain embodiments, the formulation is in liquid form and has minimized risk of bubble formation and anaphylactoid side effects. In certain embodiments, the formulation is isotonic. In certain embodiments, the formulation has a pH of 6.8 to 7.4.

Examples of pharmaceutically acceptable carriers include, but are not limited to, phosphate buffered saline solution, sterile water (including water for injection USP), emulsions such as oil/water emulsion, and various types of wetting agents. Preferred diluents for aerosol or parenteral administration are phosphate buffered saline or normal (0.9%) saline, for example 0.9% sodium chloride solution, USP. Compositions comprising such carriers are formulated by well-known conventional methods (see, e.g., Remington, The Science and Practice of Pharmacy. 22nd edition, Pharmaceutical Press (2012), the contents of which are hereby incorporated by reference herein in their entirety). In non-limiting examples, a carrier can comprise one or more of dibasic sodium phosphate, potassium chloride, monobasic potassium phosphate, polysorbate 80 (e.g., 2-[2-[3,5-bis(2-hydroxyethoxy)oxolan-2-yl]-2-(2-hydroxyethoxy)ethoxy] ethyl (E)-octadec-9-enoate), disodium edetate dehydrate, sucrose, monobasic sodium phosphate monohydrate, and dibasic sodium phosphate dihydrate.

In certain embodiments, the formulations provided herein may be lyophilized or provided in any suitable forms including, but not limited to, injectable solutions or inhalable solutions, gel forms, and tablet forms.

In certain embodiments, the formulations provided herein are substantially pure with regard to the antibody or antigen-binding fragment thereof, meaning that at least 60% to 75% of a sample of the formulation exhibits a single species of the antibody or fragment. In certain of these embodiments, more than 60%, more than 70%, more than 80%, more than 90%, more than 95%, more than 99%, more than 99.5%, more than 99.9%, or 100% of the antibody or antigen-binding fragment thereof is a single species. Purity may be tested by a number of methods well known in the art, including for example polyacrylamide gel electrophoresis or HPLC.

Kits

Provided herein in certain embodiments are kits comprising an antibody or antigen-binding fragment thereof as provided herein. In certain embodiments, these kits further comprise instructions for use. These kits may be used, for example, to inhibit CEACAM1 activity in a cell or subject, detect CEACAM1 in a cell, subject, or biological sample, treat a condition associated with CEACAM1 activity or expression, including cancer, or inhibit CEACAM1-mediated T cell suppression in a subject in need thereof.

METHODS OF USE

Provided herein in certain embodiments are methods of inhibiting CEACAM1 activity comprising contacting CEACAM1 with an antibody or antigen-binding fragment thereof as provided herein, or a formulation comprising the antibody or antigen-binding fragment thereof, in an amount sufficient to inhibit CEACAM1 activity, such that said contacting results in a decrease in CEACAM1 activity. The decrease in activity may be partial or complete, and in certain embodiments the extent of inhibition may vary based on the amount of antibody or antigen-binding fragment.

Provided herein in certain embodiments is the use of the antibodies or antigen-binding fragments thereof as provided herein, or formulations or kits comprising these antibodies or fragments, to inhibit CEACAM1 activity.

Provided herein in certain embodiments are methods of inhibiting CEACAM1 activity in a cell comprising contacting the cell with an antibody or antigen-binding fragment thereof as provided herein, or a formulation comprising the antibody or fragment thereof, in an amount sufficient to inhibit CEACAM1 activity in the cell, such that said contacting results in a decrease in CEACAM1 activity in the cell. The decrease in activity may be partial or complete, and in certain embodiments the extent of inhibition may vary based on the amount of antibody or antigen-binding fragment. In certain embodiments, the inhibition results in a decrease in CEACAM1-modulated production of one or more cytokines by the cell, and in certain of these embodiments the cytokines are selected from the group consisting of IFN-7, IL-2, IL-17A, IL-17F, IL-6, IL-9, or TNF-α. Accordingly, also provided herein are methods of decreasing CEACAM1-modulated production of one or more cytokines in a cell comprising contacting the cell with an antibody or antigen-binding fragment thereof as provided herein, or a formulation comprising the antibody or antigen-binding fragment thereof, in an amount sufficient to inhibit CEACAM1 activity. In certain of these embodiments, the cytokines are selected from the group consisting of IFN-7, IL-2, IL-17A, IL-17F, IL-6, IL-9, or TNF-α.

Provided herein in certain embodiments is the use of the antibodies or antigen-binding fragments thereof as provided herein, or formulations or kits comprising these antibodies or fragments, to inhibit CEACAM1 activity and/or to inhibit CEACAM1-modulated production of one or more cytokines, including but not limited to IFN-7, IL-2, IL-17A, IL-17F, IL-6, IL-9, or TNF-α, in a cell.

Provided herein in certain embodiments are methods of inhibiting CEACAM1 activity in a subject comprising administering to the subject an antibody or antigen-binding fragment thereof as provided herein, or a formulation comprising the antibody or antigen-binding fragment thereof, in an amount sufficient to inhibit CEACAM1 activity in the subject. The decrease in activity may be partial or complete, and in certain embodiments the extent of inhibition may vary based on the amount of antibody or antigen-binding fragment administered. In certain embodiments, inhibition may be localized, e.g., region, organ, or cell-specific. In other embodiments, inhibition may be systemic. In certain embodiments, the subject has been diagnosed with, is suspect of having, or has been deemed at risk of developing a condition associated with CEACAM1 activity or expression, including for example a cancer or neoplasm. In certain embodiments, administration of the antibody or antigen-binding fragment thereof or the formulation results in a decrease in CEACAM1-modulated production of one or more cytokines in the subject, and in certain of these embodiments the cytokines are selected from the group consisting of IFN-7, IL-2, IL-17A, IL-17F, IL-6, IL-9, or TNF-α. Accordingly, also provided herein are methods of decreasing CEACAM1-modulated production of one or more cytokines in a subject comprising administering to the subject an antibody or antigen-binding fragment thereof as provided herein, or a formulation comprising the antibody or antigen-binding fragment thereof. In certain of these embodiments, the cytokines are selected from the group consisting of IFN-7, IL-2, IL-17A, IL-17F, IL-6, IL-9, or TNF-α.

Provided herein in certain embodiments is the use of the antibodies or antigen-binding fragments thereof as provided herein, or formulations or kits comprising these antibodies or fragments, to inhibit CEACAM1 activity in a subject, or in the manufacture of a medicament for inhibiting CEACAM1 activity and/or inhibiting CEACAM1-modulated production of one or more cytokines, including but not limited to IFN-7, IL-2, IL-17A, IL-17F, IL-6, IL-9, or TNF-α, in a subject.

Provided herein in certain embodiments are methods of inhibiting CEACAM1-modulated cytokine production by a mature dendritic cell or T cell in a subject comprising administering to the subject a therapeutically effective amount of an antibody or antigen-binding fragment thereof as provided herein, or a formulation comprising the antibody or antigen-binding fragment thereof.

Provided herein in certain embodiments is the use of the antibodies or antigen-binding fragments thereof as provided herein, or formulations or kits comprising these antibodies or fragments, to inhibit CEACAM1-modulated cytokine production by a mature dendritic cell or T cell in a subject, or in the manufacture of a medicament for inhibiting CEACAM1-modulated cytokine production by a mature dendritic cell or T cell in a subject.

Provided herein in certain embodiments are methods of inhibiting CEACAM1-mediated T cell suppression in a subject in need thereof comprising administering to the subject a therapeutically effective amount of an antibody or antigen-binding fragment thereof as provided herein, or a formulation comprising the antibody or antigen-binding fragment thereof. Inhibition of CEACAM1-mediated T cell suppression may be partial or complete, and in certain embodiments the extent of the inhibition may vary based on the amount of antibody or antigen-binding fragment administered.

Provided herein in certain embodiments is the use of the antibodies or antigen-binding fragments thereof as provided herein, or formulations or kits comprising these antibodies or fragments, to inhibit CEACAM1-mediated T cell suppression in a subject in need thereof, or in the manufacture of a medicament for inhibiting CEACAM1-mediated T cell suppression in a subject in need thereof.

Provided herein in certain embodiments are methods of treating a condition associated with CEACAM1 activity or expression in a subject in need thereof comprising administering to the subject a therapeutically effective amount of an antibody or antigen-binding fragment thereof as provided herein, or a formulation comprising the antibody or antigen-binding fragment thereof. In certain of these embodiments, the condition associated with CEACAM1 activity or expression is cancer.

Provided herein in certain embodiments is the use of the antibodies or antigen-binding fragments thereof as provided herein, or formulations or kits comprising these antibodies or fragments, to treat a condition associated with CEACAM1 activity or expression in a subject in need thereof, or in the manufacture of a medicament for treating a condition associated with CEACAM1 activity or expression in a subject in need thereof.

Provided herein in certain embodiments are methods of treating cancer in a subject in need thereof comprising administering to the subject a therapeutically effective amount of an antibody or antigen-binding fragment thereof as provided herein, or a formulation comprising the antibody or antigen-binding fragment thereof. In certain of these embodiments, the cancer is a solid malignancy, and in certain embodiments the cancer comprises a solid tumor. In certain embodiments, the cancer is head and neck squamous cell carcinoma, kidney renal clear cell carcinoma, kidney renal papillary cell carcinoma, or brain lower grade glioma. In certain embodiments, the cancer is pancreatic, colorectal, stomach, melanoma, liver, bile duct, urinary tract, lung, lymphoma, upper aerodigestive, breast, thyroid, esophageal, or ovarian cancer. In certain embodiments, the cancer is leukemia or medulloblastoma. In certain embodiments, the subject is currently receiving or has previously received anti-PD-1, anti-PD-L1, or anti-CTLA4 therapy. In certain of these embodiments, the subject is treated with a combination of an antibody or antigen-binding fragment thereof or pharmaceutical formulation as provided herein and anti-PD-1, anti-PD-L1, or anti-CTLA4 therapy. In these embodiments, the agents may be administered simultaneously or sequentially, and at the same or different dosage intervals.

Provided herein in certain embodiments is the use of the antibodies or antigen-binding fragments thereof as provided herein, or formulations or kits comprising these antibodies or fragments, to treat cancer in a subject in need thereof, or in the manufacture of a medicament for treating cancer in a subject in need thereof.

Provided herein in certain embodiments are methods of interfering with the interaction between or among IgV domains of multiple CEACAM1 proteins comprising contacting a sample comprising multiple CEACAM1 proteins with an antibody or antigen-binding fragment thereof as provided herein, or a formulation comprising the antibody or antigen-binding fragment thereof.

Provided herein in certain embodiments is the use of the antibodies or antigen-binding fragments thereof as provided herein, or formulations or kits comprising these antibodies or fragments, to interfere with the interaction between or among IgV domains of multiple CEACAM1 proteins, or in the manufacture of a medicament for interfering with the interaction between or among IgV domains of multiple CEACAM1 proteins.

Provided herein in certain embodiments are methods of detecting CEACAM1 expression in a cell comprising contacting the cell with an antibody or antigen-binding fragment thereof as provided herein, or a formulation comprising the antibody or antigen-binding fragment thereof, wherein the antibody or antigen-binding fragment thereof is linked or conjugated to a detectable marker, and then detecting the marker to determine whether the antibody or antigen-binding fragment is bound to the cell, said binding indicating the presence of CEACAM1 expression.

Provided herein in certain embodiments are methods of detecting CEACAM1 expression in a subject comprising administering to the subject an antibody or antigen-binding fragment thereof as provided herein, or a formulation comprising the antibody or antigen-binding fragment thereof, wherein the antibody or antigen-binding fragment thereof is linked or conjugated to a detectable marker, and then detecting the marker to determine whether CEACAM1 expression is present. In certain embodiments, these methods are used to detect the presence of a CEACAM1-expressing cancer cell. Accordingly, provided herein in certain embodiments are methods of diagnosing a CEACAM1-expressing cancer in a subject.

Provided herein in certain embodiments is the use of the antibodies or antigen-binding fragments thereof as provided herein, or formulations or kits comprising these antibodies or fragments, to detect CEACAM1 expression in a subject, including detecting CEACAM1 expression in order to detect a CEACAM1-expressing cancer.

Provided herein in certain embodiments are methods of labeling CEACAM1 comprising contacting CEACAM1 with an antibody or antigen-binding fragment thereof linked or conjugated to a detectable marker.

Nucleic Acids, Vectors, and Host Cells

Provided herein are nucleic acid molecules comprising a nucleic acid sequence encoding an antibody or antigen-binding fragment thereof provided herein. Also provided herein are vectors comprising one or more of the nucleic acid molecules provided herein, and host cells comprising one or more of the nucleic acid molecules or vectors provided herein.

In certain embodiments, the nucleic acid molecules provided herein comprise a nucleic acid sequence encoding an antibody or antigen-binding fragment thereof comprising:

(a) a heavy chain variable region comprising one or more of:

```
                                   (SEQ ID NO: 13)
    GYIFRNYGMN, (SEQ ID NO: 14)
    WINTYTGEPTYADDFKG,
    and (SEQ ID NO: 15)
    RGWLLTGGAMDY;
```

(b) a light chain variable region comprising one or more of:

```
                                   (SEQ ID NO: 16)
    RASQDIGSSLN, (SEQ ID NO: 17)
    ATSSLDS,
    and (SEQ ID NO: 18)
    LQYVSSPWT;
```

(c) a heavy chain variable region comprising one or more of:

```
                                   (SEQ ID NO: 19)
    GYIFRNYGMN, (SEQ ID NO: 20)
    WINTYTGEPTYADDFKG,
    and (SEQ ID NO: 21)
    DCGTSHYYAMDY;
```

(d) a light chain variable region comprising one or more of:

```
                                   (SEQ ID NO: 22)
    RASQDISNYLN,
```

YTSRLHS, and (SEQ ID NO: 23)

QQGNTFPLT; (SEQ ID NO: 24)

(e) a heavy chain variable region comprising one or more of:

GYAFTIYLIE, (SEQ ID NO: 25)

VINPGSGGTNYNEKFKG, and (SEQ ID NO: 26)

SYYYGSFAMDY; (SEQ ID NO: 27)

(f) a light chain variable region comprising one or more of:

RASQDIGNYLN, (SEQ ID NO: 28)

YTSRLHS, and (SEQ ID NO: 29)

QQGNTLRT. (SEQ ID NO: 30)

In certain embodiments, the nucleic acid molecules provided herein comprise a nucleic acid sequence encoding an antibody or antigen-binding fragment thereof comprising:

(a) an antibody heavy chain variable region comprising one or more of:

GYIFRNYGMN, (SEQ ID NO: 13)

WINTYTGEPTYADDFKG, and (SEQ ID NO: 14)

RGWLLTGGAMDY; (SEQ ID NO: 15)

an antibody heavy chain variable region comprising one or more of:

GYIFRNYGMN, (SEQ ID NO: 19)

WINTYTGEPTYADDFKG, and (SEQ ID NO: 20)

DCGTSHYYAMDY; (SEQ ID NO: 21)

(b) an antibody heavy chain variable region comprising one or more of:

GYAFTIYLIE, (SEQ ID NO: 25)

VINPGSGGTNYNEKFKG, and (SEQ ID NO: 26)

SYYYGSFAMDY; (SEQ ID NO: 27)

an antibody light chain variable region comprising one or more of:

RASQDIGSSLN, (SEQ ID NO: 16)

ATSSLDS, and (SEQ ID NO: 17)

LQYVSSPWT; (SEQ ID NO: 18)

(c) an antibody light chain variable region comprising one or more of:

RASQDISNYLN, (SEQ ID NO: 22)

YTSRLHS, and (SEQ ID NO: 23)

QQGNTFPLT; (SEQ ID NO: 24)

an antibody light chain variable region comprising one or more of:

RASQDIGNYLN, (SEQ ID NO: 28)

YTSRLHS, and (SEQ ID NO: 29)

QQGNTLRT. (SEQ ID NO: 30)

In certain embodiments, the nucleic acid molecules provided herein comprise a nucleic acid sequence encoding:
(a) a heavy chain variable region comprising SEQ ID NO:2;
(b) a light chain variable region comprising SEQ ID NO:4;
(c) a heavy chain variable region comprising SEQ ID NO:6;
(d) a light chain variable region comprising SEQ ID NO:8;
(e) a heavy chain variable region comprising SEQ ID NO:10; or
(f) a light chain variable region comprising SEQ ID NO:12.

In certain embodiments, the nucleic acid molecules provided herein comprise a nucleic acid sequence encoding:
(a) a heavy chain variable region comprising SEQ ID NO:2 and a light chain variable region comprising SEQ ID NO:4;
(b) a heavy chain variable region comprising SEQ ID NO:6 and a light chain variable region comprising SEQ ID NO:8; or
(c) a heavy chain variable region comprising SEQ ID NO:10 and a light chain variable region comprising SEQ ID NO:12.

In certain embodiments, the nucleic acid molecules provided herein comprise a nucleic acid sequence having the sequence set forth in any of SEQ ID NOs:1, 3, 5, 7, 9, or 11.

In certain embodiments, the nucleic acid molecules provided herein are DNA molecules, and in certain of these embodiments the DNA molecules are cDNA molecules. In other embodiments, the nucleic acid molecules provided herein are RNA molecules.

Provided herein in certain embodiments are methods of producing an antibody or antigen-binding fragment thereof as provided herein comprising culturing a host cell as provided herein under conditions in which the antibody or antigen-binding fragment thereof is expressed.

Fusion Proteins

Provided herein in certain embodiments are fusion proteins comprising one or more antibodies or antigen-binding fragments provided herein, as well as nucleic acids encoding these fusion proteins, vectors comprising these nucleic acids, host cells comprising these vectors, and methods of expressing fusion proteins from these host cells. Also provided herein are methods of use are nucleic acid molecules comprising a nucleic acid sequence encoding an antibody or antigen-binding fragment thereof provided herein. Also provided herein are vectors comprising one or more of the nucleic acid molecules provided herein, and host cells comprising one or more of the nucleic acid molecules or vectors provided herein.

All combinations of the various elements described herein are within the scope of the technology unless otherwise indicated herein or otherwise clearly contradicted by context.

When introducing elements of the present technology or the preferred embodiment(s) thereof, the articles "a", "an", "the" and "said" are intended to mean that there are one or more of the elements.

Throughout this disclosure, various aspects of this technology are presented in a range format. It should be understood that the description in range format is merely for convenience and brevity and should not be construed as an inflexible limitation on the scope of the technology. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Other objects, advantages and features of the present technology will become apparent from the following specification taken in conjunction with the accompanying drawings.

The disclosures of all publications, patents, patent application publications and books referred to herein, are hereby incorporated by reference in their entirety into the subject application to more fully describe the art to which the subject technology pertains.

This technology may be better understood from the Experimental Details, which follow.

EXAMPLES

Example 1: Identification of CEACAM1 Expression in Human Cancers

Figure 1B:
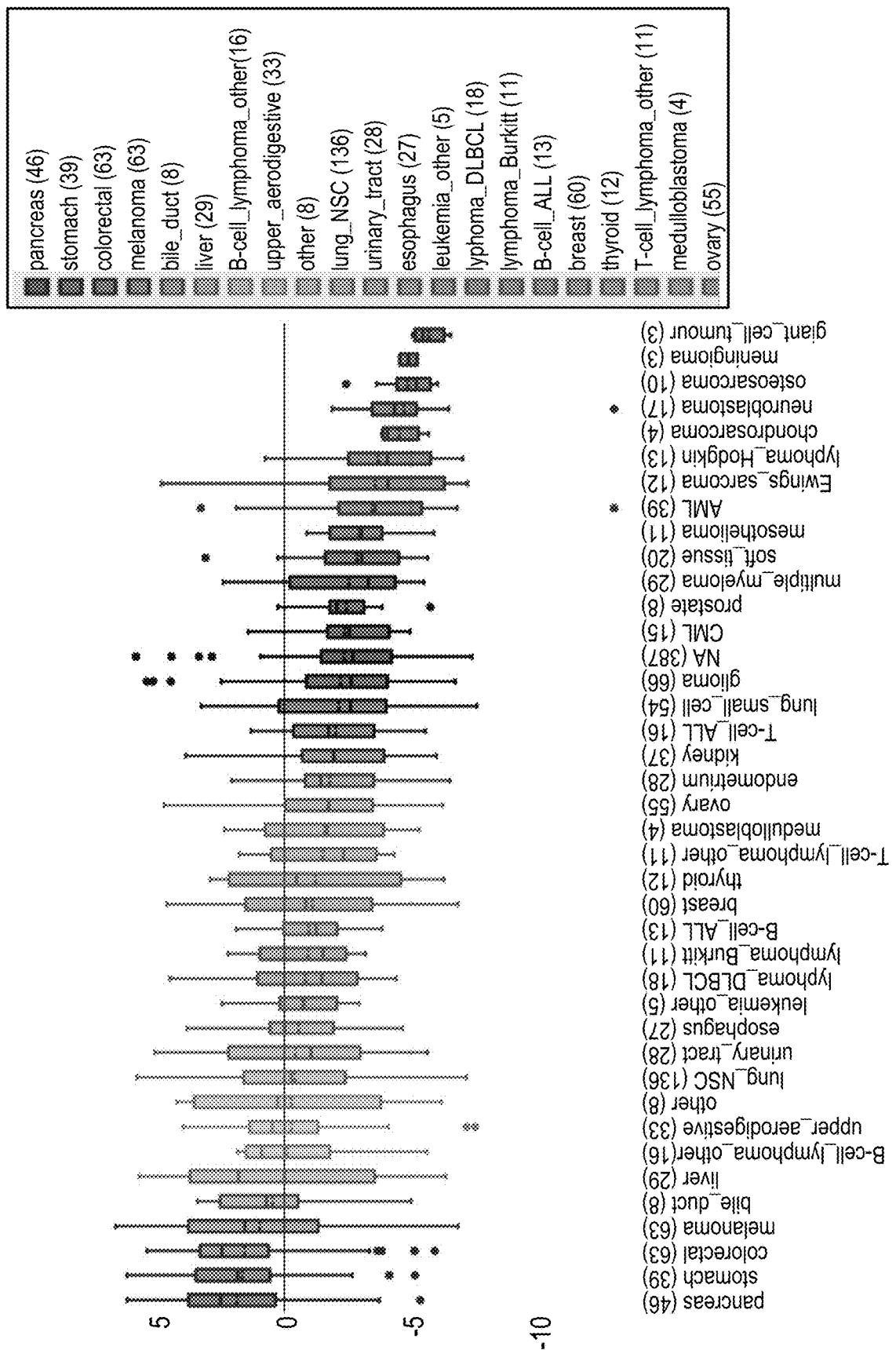
Figure 2:
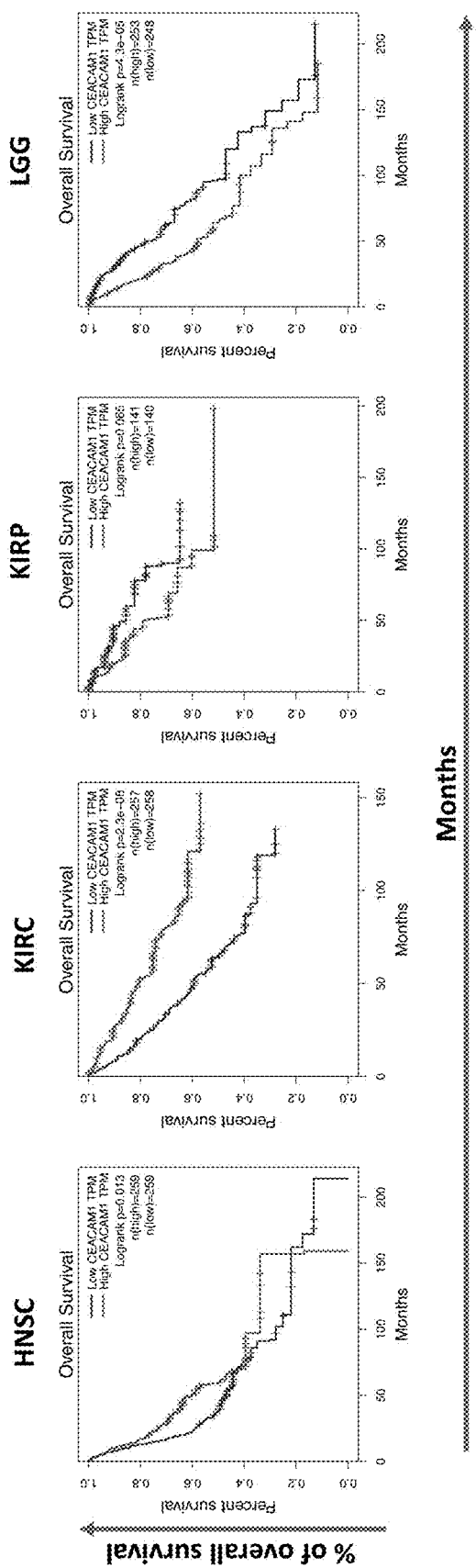
FIG. 2. Higher levels of CEACAM1 in the tumor microenvironment are significantly associated with lower overall survival of patients with HNSC (Head and neck squamous cell carcinoma), KIRC (Kidney renal clear cell carcinoma), KIRP (Kidney renal papillary cell carcinoma), or LGG (Brain lower grade glioma).

Through analysis of microarray and RNA-sequencing datasets, it was determined that CEACAM1 is widely expressed in many human cancer lines from pancreas, colorectal, stomach, melanoma, liver, bile duct, urinary tract, lung, lymphoma, upper aerodigestive, breast, thyroid, esophagus, leukemia, ovary, and medulloblastoma (FIG. 1). Higher levels of CEACAM1 were also found to be significantly associated with lower overall survival of patients with HNSC (Head and neck squamous cell carcinoma), KIRC (Kidney renal clear cell carcinoma), KIRP (Kidney renal papillary cell carcinoma), or LGG (Brain lower grade glioma) (FIG. 2). Without being bound by any theory, these findings suggest that human cancer uses CEACAM1 as an immune checkpoint to inhibit anti-tumor immunity.

Example 2: Generation of Monoclonal Antibody that Specifically Bind the IgV Domain of Human CEACAM1

Since the IgV domain is the functional domain of CEACAM1, monoclonal antibodies that specifically bind this domain were generated. A human CEACAM1 IgV-Ig fusion protein was generated by fusing the CEACAM1 IgV coding region (L36-S150) to a human IgG1 Fc tag of plasmid pMT/BiP as previously described (Zhao 2013). The fusion protein was expressed in an S2 system and then purified. Mice were immunized with the fusion protein, and hybridomas were generated by standard techniques from splenocytes fused to NS0 myeloma cells.

Example 3: Characterization of CEACAM1 Monoclonal Antibodies

Figures 4A, 4B:
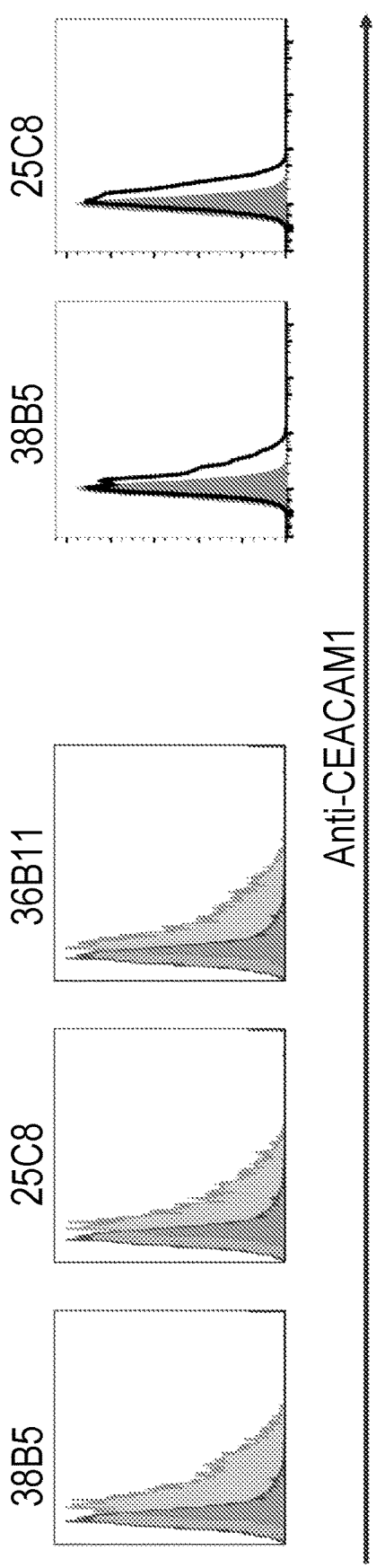
FIGS. 4A-4B. FACS shows mAbs 38B5, 25C8, and 36B11 recognize endogenous CEACAM1 expressed on human T cells (A) or human Dendritic cells (B).
Figure 5:
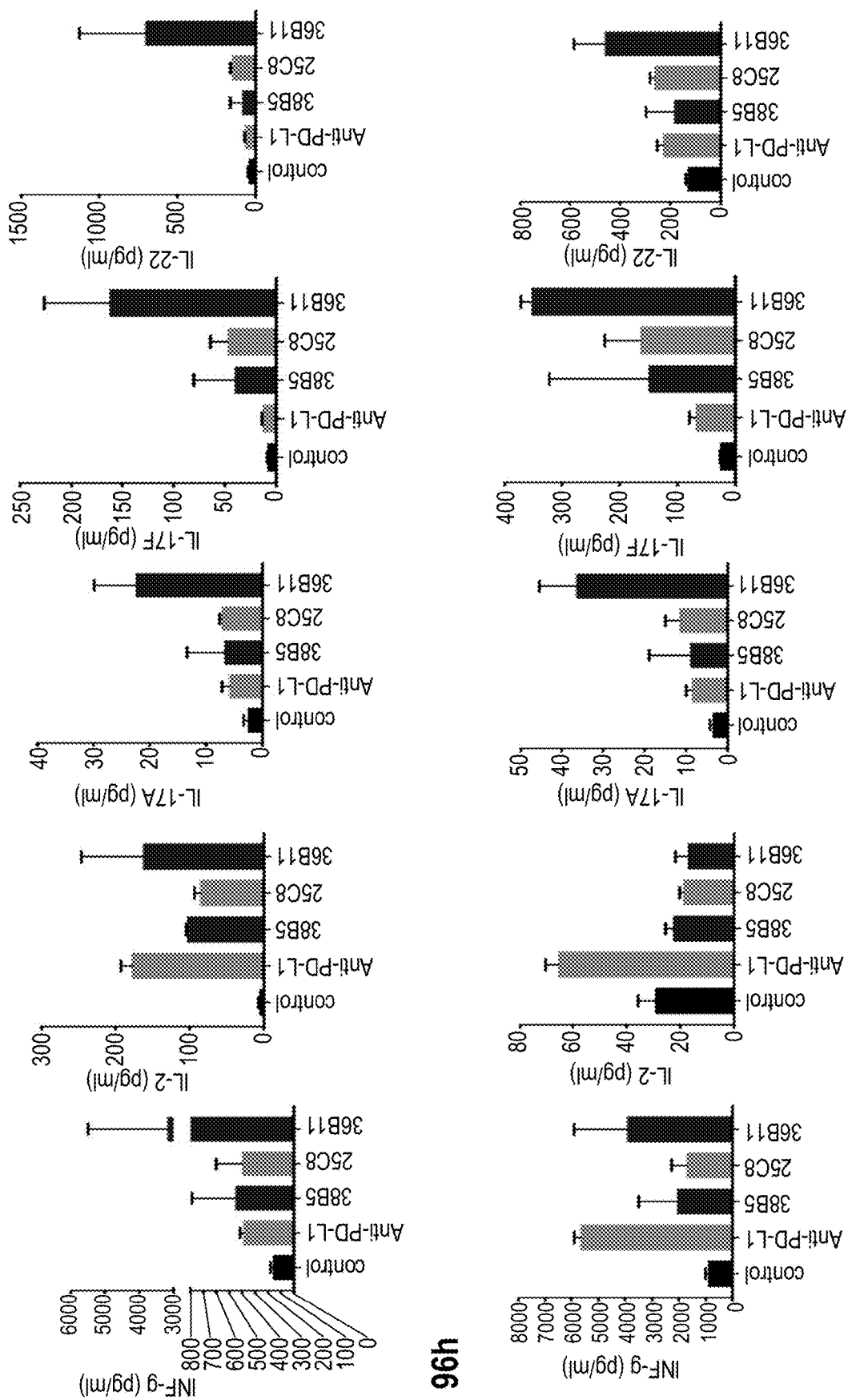
FIG. 5. mAbs 36B111, 38B5, and 25C8 significantly increase various cytokine production on 48 hours or 96 hours in mixed lymphocyte reaction assay.

Ten IgG1 antibodies with kappa chain generated as described in Example 2 were evaluated for CEACAM1 binding using Surface Plasmon Resonance. The ten antibodies exhibited binding affinities ranging from 0.589 to 93.1 nM $K_D$ (FIG. 3). Three of the antibodies, 36B11, 38B5, and 25C8, were found to recognize endogenous CEACAM1 expressed on human T cells or human dendritic cells (FIG. 4). These three antibodies were evaluated for blocking function using a mixed lymphocyte reaction. Mature dendritic cells differentiated from monocytes from PBMC from one donor were incubated with purified T cells from PBMC from another donor for four days. The mixed lymphocyte reaction was evaluated for 36B11, 38B5, and 25C8, with mouse IgG1 as the negative control and anti-PD-L1 as the positive control. All three CEACAM1 antibodies significantly increased production of various cytokines, including IFN-γ, IL-2, IL-17A, IL-17F, IL-6, IL-9, and TNF-α, at 48 hours or 96 hours (FIG. 5).

Taken together, these results demonstrate that the monoclonal antibodies 36B11, 38B5, and 25C8 are antagonist antibodies against human CEACAM1.

Example 4: Antibody Sequencing

Figure 6:
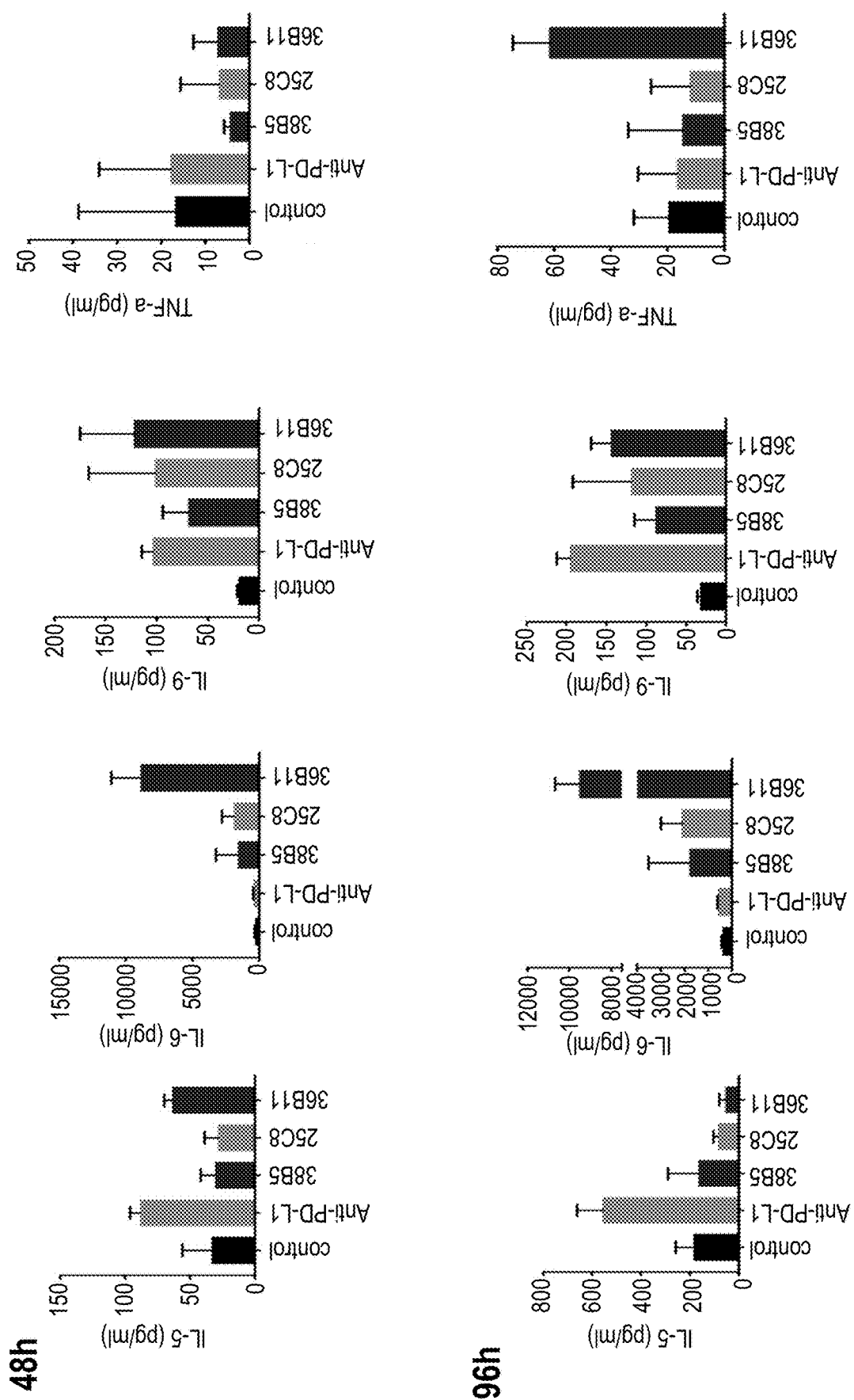
FIG. 6. mAbs 36B111, 38B5, and 25C8 significantly increase various cytokine production on 48 hours or 96 hours in mixed lymphocyte reaction assay.

Antibody 38B5, 36B11, and 25C8 hybridomas were sequenced, and all three were found to be different clones with unique VH and VL sequences (FIG. 6). The DNA and amino acid sequences of the heavy and light chains of each of these antibodies are set forth below. Leader sequences are in italics, CDR sequences are underlined. Non-italicized and non-underlined portions are framework sequences.

38B5 heavy chain DNA coding sequence (420 bp):

(SEQ ID NO: 1)
*ATGGATTGGGTGTGGACCTTGCCATTCCTGATGGCAGCTGCCCAAAGTGCC*

CAAGCACAGATCCAGTTGGTGCAGTCTGGACCTGAGCTGAAGAAGCCTGGA

GAGACAGTCAAGATCTCCTGCAAGGCTTCTGGGTATATCTTCAGAAACTAT

GGAATGAACTGGGTGAAGCAGGCTCCAGGAAAGGGTTTAAAGTGGATGGGC

TGGATAAACACCTACACTGGAGAGCCAACATATGCTGATGACTTCAAGGGA

CGGTTTGCCTTCTCTTTGGAAACCTCTGCCAGCACTGCCTATTTGCAGATC

AACAACCTCAAAAATGAGGACATGGCTACATATTTCTGTGCAAGACGGGGA

TGGTTACTTACTGGGGGTGCTATGGACTACTGGGGTCAAGGAACCTCAGTC

ACCGTCTCTCAG.

38B5 heavy chain amino acid sequence (140 AA):

(SEQ ID NO: 2)
MDWVWTLPFLMAAAQSAQAQIQLVQSGPELKKPGETVKISCKASGYIFRNY

GMNWVKQAPGKGLKWMGWINTYTGEPTYADDFKGRFAFSLETSASTAYLQI

NNLKNEDMATYFCARRGWLLTGGAMDYWGQGTSVTVSQ.

38B5 heavy chain CDR1: GYIFRNYGMN (SEQ ID NO:13).
38B5 heavy chain CDR2: WINTYTGEPTYADDFKG (SEQ ID NO:14).
38B5 heavy chain CDR3: RGWLLTGGAMDY (SEQ ID NO:15).
38B5 light chain coding sequence (389 bp):

(SEQ ID NO: 3)
ATGAGGGCCCCTGCTCAGATTTTTGGGTTCTTGTTGCTCTTGTTTCCAGGT

ACCAGATGTGACATCCAGATGACCCAGTCTCCATCCTCCTTATCTGCCTCT

CTGGGAGAAAGAGTCAGTCTCACTTGTCGGGCAAGTCAGGACATTGGTAGT

AGCTTAAACTGGCTTCAGCAGGAACCAGATGGAACTATTAAACGCCTGATC

TACGCCACATCCAGTTTAGATTCTGGTGTCCCCAAAAGGTTCAGTGGCAGT

AGGTCTGGGTCAGATTATTCTCTCACCATCAGCAGCCTTGAGTCTGAAGAT

TTTGTAGACTATTACTGTCTACAATATGTTAGTTCTCCGTGGACGTTCGGT

GGAGGCACCAAGCTGGAAATCAAACGGGCTGA.

38B5 light chain amino acid sequence (129 AA):

(SEQ ID NO: 4)
MRAPAQIFGFLLLLFPGTRCDIQMTQSPSSLSASLGERVSLTCRASQDIGS

SLNWLQQEPDGTIKRLIYATSSLDSGVPKRFSGSRSGSDYSLTISSLESED

FVDYYCLQYVSSPWTFGGGTKLEIKRA.

38B5 light chain CDR1: RASQDIGSSLN (SEQ ID NO:16).
38B5 light chain CDR2: ATSSLDS (SEQ ID NO:17).
38B5 light chain CDR3: LQYVSSPWT (SEQ ID NO:18).
36B11 heavy chain DNA coding sequence (404 bp):

(SEQ ID NO: 5)
ATGGATTGGGTGTGGACCTTGCCATTCCTGATGGCAGCTGCCCAAAGTGCC

CAAGCACAGATCCAGTTGGTGCAGTCTGGACCTGACCTGAAGAAGCCTGGA

GAGACAGTCAAGATCTCCTGCAAGGCTTCTGGGTATATCTTCAGAAACTAT

GGAATGAACTGGGTGAAGCAGGCTCCAGGAAAGGGTTTAAAGTGGATGGGC

TGGATAAACACCTACACTGGAGAGCCAACATATGCTGATGACTTCAAGGGA

CGGTTTGCCTTCTCTTTGGAAACCTCTGCCAGCACTGCCTATTTGCAGATC

AACAACCTCAAAAATGAGGACATGGCTACATATTTCTGTGCAAGAGACTGC

GGTACTAGCCATTACTATGCTATGGACTACTGGGGTCAAGGAACCTC.

36B11 heavy chain amino acid sequence (134 AA):

(SEQ ID NO: 6)
MDWVWTLPFLMAAAQSAQAQIQLVQSGPDLKKPGETVKISCKASGYIFRNY

GMNWVKQAPGKGLKWMGWINTYTGEPTYADDFKGRFAFSLETSASTAYLQI

NNLKNEDMATYFCARDCGTSHYYAMDYWGQGT.

36B11 heavy chain CDR1: GYIFRNYGMN (SEQ ID NO:19).
36B11 heavy chain CDR2: WINTYTGEPTYADDFKG (SEQ ID NO:20).
36B11 heavy chain CDR3: DCGTSHYYAMDY (SEQ ID NO:21).
36B11 light chain DNA coding sequence (395 bp):

(SEQ ID NO: 7)
ATGGTGTCCTCACCTCAGTTCCTTGGTCTCCTGTTGCTCTGTTTTCAAGGT

ACCAGATGTGATATCCAGATGACACAGACTACATCCTCCCTGTCTGCCTCT

CTGGGAGACAGAGTCACCATCAGTTGCAGGGCAAGTCAGGACATTAGCAAT

TATTTAAACTGGTATCAGCAGAAACCAGATGGAACTGTTAAACTCCTGATC

TACTACACATCAAGATTACACTCAGGAGTCCCATCAAGGTTCAGTGGCAGT

GGGTCTGGAACAGATTATTCTCTCTCCATTAGCAACCTGGAGCAAGAAGAT

ATTGCCACTTACTTTTGCCAACAGGGTAATACGTTTCCGCTCACGTTCGGT

GCTGGGACCAAGCTGGATCTGAAACGGGCTGATGCTGC.

36B11 light chain amino acid sequence (131 AA):

(SEQ ID NO: 8)
MVSSPQFLGLLLLLCFQGTRCDIQMTQTTSSLSASLGDRVTISCRASQDISN

YLNWYQQKPDGTVKLLIYYTSRLHSGVPSRFSGSGSGTDYSLSISNLEQED

IATYFCQQGNTFPLTFGAGTKLDLKRADA.

36B11 light chain CDR1: RASQDISNYLN (SEQ ID NO:22).
36B11 light chain CDR2: YTSRLHS (SEQ ID NO: 23).
36B11 light chain CDR3: QQGNTFPLT (SEQ ID NO: 24).
25C8 heavy chain DNA coding sequence (417 bp):

(SEQ ID NO: 9)
ATGGAATGGAGCTGGGTTTTTCTCTTTCTCCTGTCAGTAACTGCAGGTGTT

CACTCCCAGGTCCAGCTGCAGCAGTCTGGAGCTGAGCTGGTAAGGCCTGGG

ACTTCAGTGAAGGTGTCCTGCAAGGCTTCTGGATACGCCTTCACTATTTAC

TTGATAGAGTGGGTAAAGCAGAGGCCTGGACAGGGCCTTGAGTGGATTGGA

GTGATTAATCCTGGAAGTGGTGGTACTAACTACAATGAGAAGTTCAAGGGC

AAGGCAACACTGACTGCAGACAAATCCTCCAGCACTGCCTTCATGCAGCTC

-continued

AGCAGCCTGACATCTGATGACTCTGCGGTTTATTTCTGTGCAAGA<u>TCTTAT</u>

<u>TACTACGGTTCCTTTGCTATGGACTAC</u>TGGGGTCAAGGAACCTCAGTCACC

GTCTCTCAG.

25C8 heavy chain amino acid sequence (139 AA):

(SEQ ID NO: 10)
MEWSWVFLFLLSVTAGVHSQVQLQQSGAELVRPGTSVKVSCKASGYAFTIY

LIEWVKQRPGQGLEWIGVINPGSGGTNYNEKFKGKATLTADKSSSTAFMQL

SSLTSDDSAVYFCARSYYYGSFAMDYWGQGTSVTVSQ.

25C8 heavy chain CDR1: GYAFTIYLIE (SEQ ID NO:25).
25C8 heavy chain CDR2: VINPGSGGTNYNEKFKG (SEQ ID NO:26).
25C8 heavy chain CDR3: SYYYGSFAMDY (SEQ ID NO:27).
25C8 light chain DNA coding sequence (392 bp):

(SEQ ID NO: 11)
ATGGTGTCCTCAGCTCAGTTCCTTGGTCTCCTGTTGCTCTGTTTTCAAGGT

ACCAGATGTGATGTCCAGATGACACAGACTATATCCTCCCTGTCTGCCTCT

CTGGGAGACAGAGTCACCATCAGTTGC<u>AGGGCAAGTCAGGACATTGGCAAT</u>

<u>TATTTAAAC</u>TGGTATCAGCAGAAACCAGATGGAACTGTTAAACTCCTGATC

TAC<u>TACACATCAAGATTACACT</u>CAGGAGTCCCATCAAGGTTCAGTGGCAGT

GGGTCTGGAACAGATTATTCTCTCACCATTAGCAACCTGGAGCAAGAAGAT

ATTGCCACTTACTTTTGC<u>CAACAGGGTAATACGCTTCGGACG</u>TTCGGTGGA

GGCACCAAGCTGGAAATCAAACGGGCTGAATGCTG.

25C8 light chain amino acid sequence (130 AA):

(SEQ ID NO: 12)
MVSSAQFLGLLLLCFQGTRCDVQMTQTISSLSASLGDRVTISC<u>RASQDIGN</u>

<u>YLN</u>WYQQKPDGTVKLLIY<u>YTSRLHS</u>GVPSRFSGSGSGTDYSLTISNLEQED

IATYFC<u>QQGNTLRT</u>FGGGTKLEIKRAEC.

25C8 light chain CDR1: RASQDIGNYLN (SEQ ID NO:28).
25C8 light chain CDR2: YTSRLHS (SEQ ID NO:29).
25C8 light chain CDR3: QQGNTLRT (SEQ ID NO:30).

In addition, the following examples are illustrative of several embodiments of the present technology.

1. An antibody or antigen-binding fragment thereof comprising
   a) a heavy chain comprising one or more of SEQ ID NO:13, SEQ ID NO: 14, and SEQ ID NO:15; and/or
   a light chain comprising one or more of SEQ ID NO:16, SEQ ID NO:17, and SEQ ID NO:18;
   b) a heavy chain comprising one or more of SEQ ID NO:19, SEQ ID NO:20, and SEQ ID NO:21; and/or
   a light chain comprising one or more of SEQ ID NO:22, SEQ ID NO:23, and SEQ ID NO:24; or
   c) a heavy chain comprising one or more of SEQ ID NO:25, SEQ ID NO:26, and SEQ ID NO:27; and/or
   a light chain comprising one or more of SEQ ID NO:28, SEQ ID NO:29, and SEQ ID NO:30.

2. An antibody or antigen-binding fragment thereof which binds to CEACAM1 and comprises:
   a) a heavy chain comprising SEQ ID NOs:13, 14, and 15; and/or
   a light chain comprising SEQ ID NOs:16, 17, and 18;

3. An antibody or antigen-binding fragment thereof which binds to CEACAM1 and comprises:
   a) a heavy chain comprising SEQ ID NOs:19, 20, and 21; and/or
   a light chain comprising SEQ ID NOs:22, 23, and 24;

4. An antibody or antigen-binding fragment thereof which binds to CEACAM1 and comprises:
   a) a heavy chain comprising SEQ ID NOs:25, 26, and 27; and/or
   a light chain comprising SEQ ID NOs:28, 29, and 30;

5. The antibody or fragment thereof of any of examples 1-4, wherein framework regions of the light chain and/or the heavy chain are human framework regions, or have 85% or more identity thereto.

6. The antibody or fragment thereof of example 5, wherein framework regions of the light chain and/or the heavy chain are human framework regions.

7. An isolated antibody or antigen-binding fragment thereof which binds to a human CEACAM1, or the IgV domain of human CEACAM1, with an affinity of 1.5 nM $K_D$ or stronger.

8. An isolated antibody or antigen-binding fragment thereof of example 7, which binds to a human CEACAM1, or the IgV domain of human CEACAM1, with an affinity of 0.75 nM $K_D$ or stronger.

9. The isolated antibody or antigen-binding fragment thereof of any of examples 1-8, which has a human sequence Fc region.

10. The isolated antibody or antigen-binding fragment thereof of any of example 7, 8 or 9, which inhibits interaction between or among the IgV domains of multiple CEACAM1 proteins or inhibits CEACAM1-modulated cytokine production by a human mature dendritic cell or human T cell.

11. The isolated antibody or antigen-binding fragment thereof of example 10, wherein the cytokine production is one or more of IFN-g, IL-2, IL-17A, IL-17F, IL-6, IL-9, or TNF-α production.

12. The isolated antibody or antigen-binding fragment thereof of any one of examples 1-11, wherein the antibody or fragment thereof is chimeric or humanized.

13. The isolated antibody or antigen-binding fragment thereof of any one of examples 1-12, wherein the antibody or fragment thereof is selected from the group consisting of a monoclonal antibody, an scFv, an Fab fragment, an Fab' fragment, an F(ab)' fragment and a bispecific antibody.

14. A nucleic acid encoding a heavy chain of an antibody which comprises one or more of SEQ ID NO:13, SEQ ID NO:14, or SEQ ID NO:15.

15. A nucleic acid encoding a heavy chain of an antibody which comprises one or more of SEQ ID NO:19, SEQ ID NO:20, or SEQ ID NO:21.

16. A nucleic acid encoding a heavy chain of an antibody which comprises one or more of SEQ ID NO:25, SEQ ID NO:26, or SEQ ID NO:27.

17. A nucleic acid encoding a light chain of an antibody which comprises one or more of SEQ ID NO:16, SEQ ID NO:17, or SEQ ID NO:18.

18. A nucleic acid encoding a light chain of an antibody which comprises one or more of SEQ ID NO:22, SEQ ID NO:23, or SEQ ID NO:24.

19. A nucleic acid encoding a light chain of an antibody which comprises one or more of SEQ ID NO:28, SEQ ID NO:29, or SEQ ID NO:30.

20. A host cell comprising one or more of the nucleic acids of any of examples 14-19.

21. An antibody or fragment thereof according to any of examples 1-13, linked or conjugated to a therapeutic agent, an imaging agent or a detectable marker.

22. The antibody or fragment thereof according to example 21, wherein the therapeutic agent is a cytotoxic drug, a radioactive isotope, an immunomodulator, or a second antibody.

23. A method of inhibiting a human CEACAM1 activity in a subject comprising administering an amount of an antibody, or fragment thereof, of any of examples 1-13, 21 or 22, or a human CEACAM1-binding fragment thereof, effective to inhibit a human CEACAM1 activity in said subject.

24. The method of example 23, wherein the subject has a cancer or a neoplasm or is suspected of having a cancer or a neoplasm.

25. A method of inhibiting CEACAM1-mediated T cell suppression in a subject comprising administering an amount of an antibody, or fragment thereof, of any of examples 1-13, 21 or 22, effective to inhibit CEACAM1-mediated T cell suppression in said subject.

26. A method of treating and/or preventing a cancer or a neoplasm in a subject comprising administering an amount of an antibody, or fragment thereof, of any of examples 1-13, 21 or 22, effective to treat a cancer or neoplasm in said subject.

27. The method of example 26, wherein the cancer is a human CEACAM1-positive cancer or neoplasm.

28. The method of example 24, 26 or 27, wherein the cancer is a hematologic malignancy.

29. The method of example 24, 26 or 27, wherein the cancer comprises a solid tumor.

30. The method of example 29, wherein the cancer is head and neck squamous cell carcinoma, kidney renal clear cell carcinoma, kidney renal papillary cell carcinoma or brain lower grade glioma.

31. The method of example 29, wherein the cancer is pancreatic, colorectal, stomach, melanoma, liver, bile duct, urinary tract, lung, lymphoma, upper aerodigestive, breast, thyroid, esophageal, or ovarian cancer, or is a leukemia or medulloblastoma.

32. The method of example 24 or 26 to 31, wherein the subject is receiving or has received an anti-PD-1 or anti-PD-L1 or anti-CTLA4 therapy.

33. A method of detecting a human CEACAM1-positive cell in a subject comprising administering an amount of an antibody or fragment thereof of any of examples 1-13 having a detectable marker conjugated thereto, in an amount effective to label a human CEACAM1-positive cell and then detecting the presence and/or quantifying the level of the label in the subject, thereby detecting a human CEACAM1-positive cell in the subject.

34. The method of example 33, wherein the label is detected by imaging.

35. The method of example 33 or 34, wherein the cell is a cancer cell or neoplastic cell.

36. An isolated anti-CEACAM1 antibody or antibody fragment that:
(a) specifically binds to the IgV domain of CEACAM1, the antibody or antibody fragment comprising a heavy chain variable region comprising the CDR sequences set forth in SEQ ID NOs: 13-15, SEQ ID NOs: 19-21 or SEQ ID NOs: 25-27; and/or a light chain variable region comprising the CDR sequences set forth in SEQ ID NOs: 16-18, SEQ ID NOs: 22-24 or SEQ ID NOs: 28-30; or (b) specifically binds to the same epitope on CEACAM1 as does a reference antibody or antibody fragment, or cross-competes for specific binding to CEACAM1 or the IgV domain of CEACAM1 with a reference antibody or antibody fragment, said reference antibody or antibody fragment comprising a heavy chain variable region comprising the CDR sequences set forth in SEQ ID NOs: 13-15, SEQ ID NOs: 19-21 or SEQ ID NOs: 25-27; and/or a light chain variable region comprising the CDR sequences set forth in SEQ ID NOs: 16-18, SEQ ID NOs: 22-24 or SEQ ID NOs: 28-30.

37. The isolated anti-CEACAM1 antibody or antibody fragment of example 36, wherein the antibody or antibody fragment inhibits or reduces interaction between or among the IgV domains of multiple CEACAM1 proteins or inhibits or reduces CEACAM1-modulated cytokine production by a mature dendritic cell or T cell in a subject.

38. The isolated antibody or antibody fragment of example 36 or 37, wherein the heavy chain variable region comprises an amino acid sequence comprising at least 85% sequence identity to SEQ ID NO: 2, optionally at least 90%, 95% or 99% sequence identity to SEQ ID NO: 2.

39. The isolated antibody or antibody fragment of example 38, wherein the heavy chain variable region comprises the amino acid sequence set forth in SEQ ID NO: 2.

40. The isolated antibody or antibody fragment of example 36 or 37, wherein the heavy chain variable region comprises an amino acid sequence comprising at least 85% sequence identity to SEQ ID NO: 6, optionally at least 90%, 95% or 99% sequence identity to SEQ ID NO: 6.

41. The isolated antibody or antibody fragment of example 40, wherein the heavy chain variable region comprises the amino acid sequence set forth in SEQ ID NO: 6.

42. The isolated antibody or antibody fragment of example 36 or 37, wherein the heavy chain variable region comprises an amino acid sequence comprising at least 85% sequence identity to SEQ ID NO: 10, optionally at least 90%, 95% or 99% sequence identity to SEQ ID NO: 10.

43. The isolated antibody or antibody fragment of example 42, wherein the heavy chain variable region comprises the amino acid sequence set forth in SEQ ID NO: 10.

44. The isolated antibody or antibody fragment of example 36 or 37, wherein the light chain variable region comprises an amino acid sequence comprising at least 85% sequence identity to SEQ ID NO: 4, optionally at least 90%, 95% or 99% sequence identity to SEQ ID NO: 4.

45. The isolated antibody or antibody fragment of example 44, wherein the light chain variable region comprises the amino acid sequence set forth in SEQ ID NO: 4.

46. The isolated antibody or antibody fragment of example 36 or 37, wherein the light chain variable region comprises an amino acid sequence comprising at least 85% sequence identity to SEQ ID NO: 8, optionally at least 90%, 95% or 99% sequence identity to SEQ ID NO: 8.

47. The isolated antibody or antibody fragment of example 46, wherein the light chain variable region comprises the amino acid sequence set forth in SEQ ID NO: 8.

48. The isolated antibody or antibody fragment of example 36 or 37, wherein the light chain variable region comprises an amino acid sequence comprising at least 85% sequence identity to SEQ ID NO: 12, optionally at least 90%, 95% or 99% sequence identity to SEQ ID NO: 12.

49. The isolated antibody or antibody fragment of example 48, wherein the light chain variable region comprises the amino acid sequence set forth in SEQ ID NO: 12.

50. A pharmaceutical composition comprising an effective amount of the antibody or antibody fragment of any of the examples 1-6, or the isolated antibody or antibody fragment of any of the examples 7-13 and 36-49, and a pharmaceutically acceptable carrier or excipient.

51. A method of interfering with interaction between or among IgV domains of multiple CEACAM1 proteins comprising contacting a sample comprising multiple CEACAM1 proteins with the isolated antibody or antibody fragment according to any of examples 36-49, thereby interfering with the interaction between or among the IgV domains of multiple CEACAM1 proteins.

52. A method of inhibiting or reducing a CEACAM1 activity in a subject comprising administering an amount of an antibody or fragment thereof of any of examples 36-49 or a pharmaceutical composition of example 50, effective to inhibit or reduce a CEACAM1 activity in a subject in the subject.

53. The method of example 52, which is used to inhibit or reduce interaction between or among the IgV domains of multiple CEACAM1 proteins in a subject.

54. The method of example 52 or 53, which is used to inhibit or reduce CEACAM1-modulated cytokine production by a mature dendritic cell or T cell in a subject.

55. The method of any of examples 52-54, which is used to prevent or treat a disease or disorder that is associated with abnormally elevated level of CEACAM1 in a subject.

56. The method of example 55, wherein the disease or disorder is a cancer or neoplasm.

57. The method of example 56, wherein the subject is receiving or has received an anti-PD-1 or anti-PD-L1 or anti-CTLA4 therapy.

58. A method of inhibiting a human CEACAM1 activity in a subject comprising administering an amount of an antibody, or fragment thereof, of any of examples 1-13, 21 or 22, effective to inhibit a human CEACAM1 activity in a subject.

59. The method of example 58, wherein the subject has a cancer or a neoplasm or is suspected of having a cancer or a neoplasm.

60. A method of inhibiting CEACAM1-mediated T cell suppression in a subject comprising administering an amount of an antibody, or fragment thereof, of any of examples 1-13, 21 or 22, effective to inhibit CEACAM1-mediated T cell suppression in a subject.

61. A method of treating a cancer or a neoplasm in a subject comprising administering an amount of an antibody, or fragment thereof, any of examples 1-13, 21 or 22, effective to treat a cancer or neoplasm in a subject.

62. The method of example 61, wherein the cancer is a human CEACAM1-positive cancer or neoplasm.

63. The method of any of examples 52-62, wherein the subject is a mammal.

64. The method of example 63, wherein the mammal is a human.

65. Use of an effective amount of an antibody or fragment thereof of any of examples 1-13 and 36-49 for the manufacture of a medicament for treating or preventing a disease or condition that is associated with an abnormally elevated level of CEACAM1 in a subject.

REFERENCES

1. Bird et al. Single-chain antigen-binding proteins. Science 242(4877):423-426 (1988)
2. Brown et al. Tumor-specific genetically engineered murine/human chimeric monoclonal antibody. Cancer Res 47(13):3577-3583 (1987)
3. Chothia & Lesk. Canonical structures for the hypervariable regions of immunoglobulins. J Mol Biol 196(4):901-917 (1987)
4. Chothia et al. Conformations of immunoglobulin hypervariable regions. Nature 342(6252):877-883 (1989)
5. Dankner et al. CEACAM1 as a multi-purpose target for cancer immunotherapy. Oncoimmunology 6(7):e1328336 (2017)
6. Daugherty et al. Polymerase chain reaction facilitates the cloning, CDR-grafting, and rapid expression of a murine monoclonal antibody directed against the CD18 component of leukocyte integrins. Nucl Acids Res 19(9):2471-2476 (1991)
7. Gray-Owen & Blumberg. CEACAM1: contact-dependent control of immunity. Nat Rev Immunol 6(6):433-446 (2006)
8. Hamers-Casterman et al. Naturally occurring antibodies devoid of light chains. Nature 363(6428):446-448 1993
9. Harris. Production of humanized monoclonal antibodies for in vivo imaging and therapy. Biochem Soc Trans 23(4):1035-1038 (1995)
10. Hurle & Gross. Protein engineering techniques for antibody humanization. Curr Opin Biotechnol 5(4):428-433 (1994)
11. Huston et al. Protein engineering of antibody binding sites: recovery of specific activity in an anti-digoxin single-chain Fv analogue produced in *Escherichia coli*. Proc Natl Acad Sci USA 85(16):5879-5883 (1988)
12. Jones et al. Replacing the complementarity-determining regions in a human antibody with those from a mouse. Nature 321(6069):522-525 (1986)
13. Lobuglio et al. Mouse/human chimeric monoclonal antibody in man: kinetics and immune response. Proc Natl Acad Sci USA 86(11):4220-4224 (1989)
14. Presta. Antibody engineering. Curr Opin Biotechnol 3(4):394-398 (1992)
15. Riechmann et al. Reshaping human antibodies for therapy. Nature 332 (6162):323-329 (1988)
16. Shaw et al. Characterization of a mouse/human chimeric monoclonal antibody (17-1A) to a colon cancer tumor-associated antigen. J Immunol 138(12):4534-4538 (1987)
17. Sheriff et al. Redefining the minimal antigen-binding fragment. Nature Struct Biol 3(9):733-736 (1996)
18. Vaswani & Hamilton. Humanized antibodies as potential therapeutic drugs. Ann Allergy Asthma Immunol 81(2):105-115 (1998)
19. Verhoeyen et al. Reshaping human antibodies: grafting an antilysozyme activity. Science 239(4847):1534-1536 (1988)
20. Winter & Milstein. Man-made antibodies. Nature 349 (6307):293-299 (1991)
21. Zhao et al. HHLA2 is a member of the B7 family and inhibits human CD4 and CD8 T-cell function. Proc Natl Acad Sci USA 110(24):9879-9884 (2013)

What is claimed is:

1. A nucleic acid molecule comprising a nucleotide sequence encoding an antibody or antigen-binding fragment thereof that specifically binds human CEACAM1 that comprises:

(a) a heavy chain variable region comprising:

GYIFRNYGMN, (SEQ ID NO: 13)

WINTYTGEPTYADDFKG, (SEQ ID NO: 14)
and

RGWLLTGGAMDY; (SEQ ID NO: 15)

and a light chain variable region comprising:

RASQDIGSSLN, (SEQ ID NO: 16)

ATSSLDS, (SEQ ID NO: 17)
and

LQYVSSPWT; (SEQ ID NO: 18)

(b) a heavy chain variable region comprising:

GYIFRNYGMN, (SEQ ID NO: 19)

WINTYTGEPTYADDFKG, (SEQ ID NO: 20)
and

DCGTSHYYAMDY; (SEQ ID NO: 21)

and a light chain variable region comprising:

RASQDISNYLN, (SEQ ID NO: 22)

YTSRLHS, (SEQ ID NO: 23)
and

QQGNTFPLT; (SEQ ID NO: 24)

or (c) a heavy chain variable region comprising:

GYAFTIYLIE, (SEQ ID NO: 25)

-continued

VINPGSGGTNYNEKFKG, (SEQ ID NO: 26)
and

SYYYGSFAMDY; (SEQ ID NO: 27)

a light chain variable region comprising:

RASQDIGNYLN, (SEQ ID NO: 28)

YTSRLHS, (SEQ ID NO: 29)
and

QQGNTLRT. (SEQ ID NO: 30)

2. The nucleic acid molecule of claim 1, wherein the nucleic acid molecule comprises a nucleic acid sequence encoding:
 (a) a heavy chain variable region comprising SEQ ID NO: 2;
 (b) a light chain variable region comprising SEQ ID NO: 4;
 (c) a heavy chain variable region comprising SEQ ID NO: 6;
 (d) a light chain variable region comprising SEQ ID NO: 8;
 (e) a heavy chain variable region comprising SEQ ID NO: 10; or
 (f) a light chain variable region comprising SEQ ID NO: 12.

3. The nucleic acid molecule of claim 2, wherein the nucleic acid molecule comprises a nucleic acid sequence encoding:
 (a) a heavy chain variable region comprising SEQ ID NO:2 and a light chain variable region comprising SEQ ID NO:4;
 (b) a heavy chain variable region comprising SEQ ID NO:6 and a light chain variable region comprising SEQ ID NO:8; or
 (c) a heavy chain variable region comprising SEQ ID NO: 10 and a light chain variable region comprising SEQ ID NO: 12.

4. The nucleic acid molecule of claim 1, wherein the nucleic acid molecule comprises a nucleotide sequence selected from the group consisting of SEQ ID NOs: 1, 3, 5, 7, 9, and 11.

5. The nucleic acid molecule of claim 1, wherein the nucleic acid molecule comprises a nucleotide sequence selected from the group consisting of SEQ ID NOs: 1, 3, 5, 7, 9, and 11 each with the portion encoding a leader sequence removed.

6. The nucleic acid molecule of claim 5, wherein the portion encoding the leader sequence of SEQ ID NO: 1 is nucleotides 1-57, wherein the portion encoding the leader sequence of SEQ ID NO: 3 is nucleotides 1-60, wherein the portion encoding the leader sequence of SEQ ID NO: 5 is nucleotides 1-57, wherein the portion encoding the leader sequence of SEQ ID NO: 7 is nucleotides 1-60, wherein the portion encoding the leader sequence of SEQ ID NO: 9 is nucleotides 1-57, and wherein the portion encoding the leader sequence of SEQ ID NO: 11 is nucleotides 1-60.

7. The nucleic acid molecule of claim 1, wherein the nucleic acid molecule is a DNA molecule or an RNA molecule.

8. The nucleic acid molecule of claim 7, wherein the DNA molecule is a cDNA molecule.

9. A host cell comprising the nucleic acid molecule of claim 1.

* * * * *

SEQUENCE LISTING

<160> NUMBER OF SEQ ID NOS: 30

<210> SEQ ID NO 1
<211> LENGTH: 420
<212> TYPE: DNA
<213> ORGANISM: Artificial Sequence
<220> FEATURE:
<223> OTHER INFORMATION: heavy chain variable region coding sequence
<220> FEATURE:
<221> NAME/KEY: misc_feature
<222> LOCATION: (1)..(57)
<223> OTHER INFORMATION: Leader sequence
<220> FEATURE:
<221> NAME/KEY: misc_feature
<222> LOCATION: (58)..(132)
<223> OTHER INFORMATION: FR1
<220> FEATURE:
<221> NAME/KEY: misc_feature
<222> LOCATION: (133)..(162)
<223> OTHER INFORMATION: heavy chain CDR1
<220> FEATURE:
<221> NAME/KEY: misc_feature
<222> LOCATION: (163)..(204)
<223> OTHER INFORMATION: FR2
<220> FEATURE:
<221> NAME/KEY: misc_feature
<222> LOCATION: (205)..(255)
<223> OTHER INFORMATION: heavy chain CDR2
<220> FEATURE:
<221> NAME/KEY: misc_feature
<222> LOCATION: (256)..(351)
<223> OTHER INFORMATION: FR3
<220> FEATURE:
<221> NAME/KEY: misc_feature
<222> LOCATION: (352)..(368)
<223> OTHER INFORMATION: heavy chain CDR3
<220> FEATURE:
<221> NAME/KEY: misc_feature
<222> LOCATION: (369)..(420)
<223> OTHER INFORMATION: FR4

<400> SEQUENCE: 1

```
atggattggg tgtggaccct tgccattcctg atggcagctg cccaaagtgc ccaagcacag      60
atccagttgg tgcagtctgg acctgagctg aagaagcctg agagacagt caagatctcc      120 tgcaaggctt ctgggtatat cttcagaaac tatggaatga actgggtgaa gcaggctcca      180
ggaaagggtt taaagtggat gggctggata aacacctaca ctggagagcc aacatatgct      240
gatgacttca agggacggtt tgccttctct ttggaaacct ctgccagcac tgcctatttg      300
cagatcaaca acctcaaaaa tgaggacatg gctacatatt tctgtgcaag acggggatgg      360
ttacttactg ggggtgctat ggactactgg ggtcaaggaa cctcagtcac cgtctctcag      420
```

<210> SEQ ID NO 2
<211> LENGTH: 140
<212> TYPE: PRT
<213> ORGANISM: Artificial Sequence
<220> FEATURE:
<223> OTHER INFORMATION: heavy chain variable region coding sequence
<220> FEATURE:
<221> NAME/KEY: misc_feature
<222> LOCATION: (1)..(19)
<223> OTHER INFORMATION: Leader sequence
<220> FEATURE:
<221> NAME/KEY: misc_feature
<222> LOCATION: (20)..(44)
<223> OTHER INFORMATION: FR1
<220> FEATURE:
<221> NAME/KEY: misc_feature
<222> LOCATION: (45)..(54)
<223> OTHER INFORMATION: heavy chain CDR1
<220> FEATURE:
<221> NAME/KEY: misc_feature
<222> LOCATION: (55)..(68)
<223> OTHER INFORMATION: FR2
<220> FEATURE:
<221> NAME/KEY: misc_feature
<222> LOCATION: (69)..(85)
<223> OTHER INFORMATION: heavy chain CDR2
<220> FEATURE:
<221> NAME/KEY: misc_feature
<222> LOCATION: (86)..(117)
<223> OTHER INFORMATION: FR3
<220> FEATURE:
<221> NAME/KEY: misc_feature
<222> LOCATION: (118)..(129)
<223> OTHER INFORMATION: heavy chain CDR3
<220> FEATURE:
<221> NAME/KEY: misc_feature
<222> LOCATION: (130)..(140)
<223> OTHER INFORMATION: FR4

<400> SEQUENCE: 2

Met Asp Trp Val Trp Thr Leu Pro Phe Leu Met Ala Ala Gln Ser
1               5                   10                  15

Ala Gln Ala Gln Ile Gln Leu Val Gln Ser Gly Pro Glu Leu Lys Lys
            20                  25                  30

Pro Gly Glu Thr Val Lys Ile Ser Cys Lys Ala Ser Gly Tyr Ile Phe
        35                  40                  45

Arg Asn Tyr Gly Met Asn Trp Val Lys Gln Ala Pro Gly Lys Gly Leu
    50                  55                  60

Lys Trp Met Gly Trp Ile Asn Thr Tyr Thr Gly Glu Pro Thr Tyr Ala
65                  70                  75                  80

Asp Asp Phe Lys Gly Arg Phe Ala Phe Ser Leu Glu Thr Ser Ala Ser
                85                  90                  95

Thr Ala Tyr Leu Gln Ile Asn Asn Leu Lys Asn Glu Asp Met Ala Thr
            100                 105                 110

Tyr Phe Cys Ala Arg Arg Gly Trp Leu Leu Thr Gly Gly Ala Met Asp
        115                 120                 125

Tyr Trp Gly Gln Gly Thr Ser Val Thr Val Ser Gln
    130                 135                 140

<210> SEQ ID NO 3
<211> LENGTH: 389
<212> TYPE: DNA
<213> ORGANISM: Artificial Sequence
<220> FEATURE:
<223> OTHER INFORMATION: light chain variable region coding sequence
<220> FEATURE:
<221> NAME/KEY: misc_feature
<222> LOCATION: (1)..(60)
<223> OTHER INFORMATION: Leader sequence
<220> FEATURE:
<221> NAME/KEY: misc_feature
<222> LOCATION: (61)..(129)
<223> OTHER INFORMATION: FR1
<220> FEATURE:
<221> NAME/KEY: misc_feature
<222> LOCATION: (130)..(162)
<223> OTHER INFORMATION: light chain CDR1
<220> FEATURE:
<221> NAME/KEY: misc_feature
<222> LOCATION: (163)..(207)
<223> OTHER INFORMATION: FR2
<220> FEATURE:
<221> NAME/KEY: misc_feature
<222> LOCATION: (208)..(228)
<223> OTHER INFORMATION: light chain CDR2
<220> FEATURE:
<221> NAME/KEY: misc_feature
<222> LOCATION: (229)..(324)
<223> OTHER INFORMATION: FR3

```
<220> FEATURE:
<221> NAME/KEY: misc_feature
<222> LOCATION: (325)..(351)
<223> OTHER INFORMATION: light chain CDR3
<220> FEATURE:
<221> NAME/KEY: misc_feature
<222> LOCATION: (352)..(389)
<223> OTHER INFORMATION: FR4

<400> SEQUENCE: 3
atgagggccc ctgctcagat ttttgggttc ttgttgctct tgtttccagg taccagatgt      60
gacatccaga tgacccagtc tccatcctcc ttatctgcct ctctgggaga aagagtcagt     120
ctcacttgtc gggcaagtca ggacattggt agtagcttaa actggcttca gcaggaacca     180
gatggaacta ttaaacgcct gatctacgcc acatccagtt tagattctgg tgtccccaaa     240
aggttcagtg gcagtaggtc tgggtcagat tattctctca ccatcagcag ccttgagtct     300
gaagattttg tagactatta ctgtctacaa tatgttagtt ctccgtggac gttcggtgga     360
ggcaccaagc tggaaatcaa acgggctga                                       389

<210> SEQ ID NO 4
<211> LENGTH: 129
<212> TYPE: PRT
<213> ORGANISM: Artificial Sequence
<220> FEATURE:
<223> OTHER INFORMATION: light chain variable region coding sequence
<220> FEATURE:
<221> NAME/KEY: misc_feature
<222> LOCATION: (1)..(20)
<223> OTHER INFORMATION: Leader sequence
<220> FEATURE:
<221> NAME/KEY: misc_feature
<222> LOCATION: (21)..(43)
<223> OTHER INFORMATION: FR1
<220> FEATURE:
<221> NAME/KEY: misc_feature
<222> LOCATION: (44)..(54)
<223> OTHER INFORMATION: light chain CDR1
<220> FEATURE:
<221> NAME/KEY: misc_feature
<222> LOCATION: (55)..(69)
<223> OTHER INFORMATION: FR2
<220> FEATURE:
<221> NAME/KEY: misc_feature
<222> LOCATION: (70)..(76)
<223> OTHER INFORMATION: light chain CDR2
<220> FEATURE:
<221> NAME/KEY: misc_feature
<222> LOCATION: (77)..(108)
<223> OTHER INFORMATION: FR3
<220> FEATURE:
<221> NAME/KEY: misc_feature
<222> LOCATION: (109)..(117)
<223> OTHER INFORMATION: light chain CDR3
<220> FEATURE:
<221> NAME/KEY: misc_feature
<222> LOCATION: (118)..(129)
<223> OTHER INFORMATION: FR4

<400> SEQUENCE: 4

Met Arg Ala Pro Ala Gln Ile Phe Gly Phe Leu Leu Leu Phe Pro
1               5                  10                  15

Gly Thr Arg Cys Asp Ile Gln Met Thr Gln Ser Pro Ser Ser Leu Ser
            20                  25                  30

Ala Ser Leu Gly Glu Arg Val Ser Leu Thr Cys Arg Ala Ser Gln Asp
        35                  40                  45

Ile Gly Ser Ser Leu Asn Trp Leu Gln Gln Glu Pro Asp Gly Thr Ile
    50                  55                  60
```

```
Lys Arg Leu Ile Tyr Ala Thr Ser Ser Leu Asp Ser Gly Val Pro Lys
 65                  70                  75                  80

Arg Phe Ser Gly Ser Arg Ser Gly Ser Asp Tyr Ser Leu Thr Ile Ser
                 85                  90                  95

Ser Leu Glu Ser Glu Asp Phe Val Asp Tyr Tyr Cys Leu Gln Tyr Val
            100                 105                 110

Ser Ser Pro Trp Thr Phe Gly Gly Gly Thr Lys Leu Glu Ile Lys Arg
        115                 120                 125

Ala

<210> SEQ ID NO 5
<211> LENGTH: 404
<212> TYPE: DNA
<213> ORGANISM: Artificial Sequence
<220> FEATURE:
<223> OTHER INFORMATION: heavy chain variable region coding sequence
<220> FEATURE:
<221> NAME/KEY: misc_feature
<222> LOCATION: (1)..(57)
<223> OTHER INFORMATION: Leader sequence
<220> FEATURE:
<221> NAME/KEY: misc_feature
<222> LOCATION: (58)..(132)
<223> OTHER INFORMATION: FR1
<220> FEATURE:
<221> NAME/KEY: misc_feature
<222> LOCATION: (133)..(162)
<223> OTHER INFORMATION: heavy chain CDR1
<220> FEATURE:
<221> NAME/KEY: misc_feature
<222> LOCATION: (163)..(204)
<223> OTHER INFORMATION: FR2
<220> FEATURE:
<221> NAME/KEY: misc_feature
<222> LOCATION: (205)..(255)
<223> OTHER INFORMATION: heavy chain CDR2
<220> FEATURE:
<221> NAME/KEY: misc_feature
<222> LOCATION: (256)..(351)
<223> OTHER INFORMATION: FR3
<220> FEATURE:
<221> NAME/KEY: misc_feature
<222> LOCATION: (352)..(387)
<223> OTHER INFORMATION: heavy chain CDR3
<220> FEATURE:
<221> NAME/KEY: misc_feature
<222> LOCATION: (388)..(404)
<223> OTHER INFORMATION: FR4

<400> SEQUENCE: 5
atggattggg tgtggacctt gccattcctg atggcagctg cccaaagtgc ccaagcacag    60
atccagttgg tgcagtctgg acctgacctg aagaagcctg agagacagt caagatctcc    120 tgcaaggctt ctgggtatat cttcagaaac tatggaatga actgggtgaa gcaggctcca    180
ggaaagggtt taaagtggat gggctggata aacacctaca ctggagagcc aacatatgct    240
gatgacttca aggacggtt tgccttctct ttggaaacct ctgccagcac tgcctatttg    300
cagatcaaca acctcaaaaa tgaggacatg gctacatatt tctgtgcaag agactgcggt    360
actagccatt actatgctat ggactactgg ggtcaaggaa cctc                    404

<210> SEQ ID NO 6
<211> LENGTH: 134
<212> TYPE: PRT
<213> ORGANISM: Artificial Sequence
<220> FEATURE:
<223> OTHER INFORMATION: heavy chain variable region coding sequence
<220> FEATURE:
<221> NAME/KEY: misc_feature
```

```
<222> LOCATION: (1)..(19)
<223> OTHER INFORMATION: Leader sequence
<220> FEATURE:
<221> NAME/KEY: misc_feature
<222> LOCATION: (20)..(44)
<223> OTHER INFORMATION: FR1
<220> FEATURE:
<221> NAME/KEY: misc_feature
<222> LOCATION: (45)..(54)
<223> OTHER INFORMATION: heavy chain CDR1
<220> FEATURE:
<221> NAME/KEY: misc_feature
<222> LOCATION: (55)..(68)
<223> OTHER INFORMATION: FR2
<220> FEATURE:
<221> NAME/KEY: misc_feature
<222> LOCATION: (69)..(85)
<223> OTHER INFORMATION: heavy chain CDR3
<220> FEATURE:
<221> NAME/KEY: misc_feature
<222> LOCATION: (86)..(117)
<223> OTHER INFORMATION: FR3
<220> FEATURE:
<221> NAME/KEY: misc_feature
<222> LOCATION: (118)..(129)
<223> OTHER INFORMATION: heavy chain CDR3
<220> FEATURE:
<221> NAME/KEY: misc_feature
<222> LOCATION: (130)..(134)
<223> OTHER INFORMATION: FR4

<400> SEQUENCE: 6

Met Asp Trp Val Trp Thr Leu Pro Phe Leu Met Ala Ala Gln Ser
1               5                   10                  15

Ala Gln Ala Gln Ile Gln Leu Val Gln Ser Gly Pro Asp Leu Lys Lys
            20                  25                  30

Pro Gly Glu Thr Val Lys Ile Ser Cys Lys Ala Ser Gly Tyr Ile Phe
        35                  40                  45

Arg Asn Tyr Gly Met Asn Trp Val Lys Gln Ala Pro Gly Lys Gly Leu
    50                  55                  60

Lys Trp Met Gly Trp Ile Asn Thr Tyr Thr Gly Glu Pro Thr Tyr Ala
65                  70                  75                  80

Asp Asp Phe Lys Gly Arg Phe Ala Phe Ser Leu Glu Thr Ser Ala Ser
                85                  90                  95

Thr Ala Tyr Leu Gln Ile Asn Asn Leu Lys Asn Glu Asp Met Ala Thr
            100                 105                 110

Tyr Phe Cys Ala Arg Asp Cys Gly Thr Ser His Tyr Tyr Ala Met Asp
        115                 120                 125

Tyr Trp Gly Gln Gly Thr
        130

<210> SEQ ID NO 7
<211> LENGTH: 395
<212> TYPE: DNA
<213> ORGANISM: Artificial Sequence
<220> FEATURE:
<223> OTHER INFORMATION: light chain variable region coding sequence
<220> FEATURE:
<221> NAME/KEY: misc_feature
<222> LOCATION: (1)..(60)
<223> OTHER INFORMATION: Leader sequence
<220> FEATURE:
<221> NAME/KEY: misc_feature
<222> LOCATION: (61)..(129)
<223> OTHER INFORMATION: FR1
<220> FEATURE:
<221> NAME/KEY: misc_feature
<222> LOCATION: (130)..(162)
<223> OTHER INFORMATION: light chain CDR1
```

<220> FEATURE:
<221> NAME/KEY: misc_feature
<222> LOCATION: (163)..(207)
<223> OTHER INFORMATION: FR2
<220> FEATURE:
<221> NAME/KEY: misc_feature
<222> LOCATION: (208)..(228)
<223> OTHER INFORMATION: light chain CDR2
<220> FEATURE:
<221> NAME/KEY: misc_feature
<222> LOCATION: (229)..(324)
<223> OTHER INFORMATION: FR3
<220> FEATURE:
<221> NAME/KEY: misc_feature
<222> LOCATION: (325)..(351)
<223> OTHER INFORMATION: light chain CDR3
<220> FEATURE:
<221> NAME/KEY: misc_feature
<222> LOCATION: (352)..(395)
<223> OTHER INFORMATION: FR4

<400> SEQUENCE: 7

```
atggtgtcct cacctcagtt ccttggtctc ctgttgctct gttttcaagg taccagatgt    60
gatatccaga tgacacagac tacatcctcc ctgtctgcct ctctgggaga cagagtcacc   120
atcagttgca gggcaagtca ggacattagc aattatttaa actggtatca gcagaaacca   180
gatggaactg ttaaactcct gatctactac acatcaagat tacactcagg agtcccatca   240
aggttcagtg gcagtgggtc tggaacagat tattctctct ccattagcaa cctggagcaa   300
gaagatattg ccacttactt ttgccaacag gtaatacgt ttccgctcac gttcggtgct   360
gggaccaagc tggatctgaa acgggctgat gctgc                              395
```

<210> SEQ ID NO 8
<211> LENGTH: 131
<212> TYPE: PRT
<213> ORGANISM: Artificial Sequence
<220> FEATURE:
<223> OTHER INFORMATION: light chain variable region coding sequence
<220> FEATURE:
<221> NAME/KEY: misc_feature
<222> LOCATION: (1)..(20)
<223> OTHER INFORMATION: Leader sequence
<220> FEATURE:
<221> NAME/KEY: misc_feature
<222> LOCATION: (21)..(43)
<223> OTHER INFORMATION: FR1
<220> FEATURE:
<221> NAME/KEY: misc_feature
<222> LOCATION: (44)..(54)
<223> OTHER INFORMATION: light chain CDR1
<220> FEATURE:
<221> NAME/KEY: misc_feature
<222> LOCATION: (55)..(69)
<223> OTHER INFORMATION: FR2
<220> FEATURE:
<221> NAME/KEY: misc_feature
<222> LOCATION: (70)..(76)
<223> OTHER INFORMATION: light chain CDR2
<220> FEATURE:
<221> NAME/KEY: misc_feature
<222> LOCATION: (77)..(108)
<223> OTHER INFORMATION: FR3
<220> FEATURE:
<221> NAME/KEY: misc_feature
<222> LOCATION: (109)..(117)
<223> OTHER INFORMATION: light chain CDR3
<220> FEATURE:
<221> NAME/KEY: misc_feature
<222> LOCATION: (118)..(131)
<223> OTHER INFORMATION: FR4

<400> SEQUENCE: 8

Met Val Ser Ser Pro Gln Phe Leu Gly Leu Leu Leu Cys Phe Gln
1               5                   10                  15

Gly Thr Arg Cys Asp Ile Gln Met Thr Gln Thr Thr Ser Ser Leu Ser
            20                  25                  30

Ala Ser Leu Gly Asp Arg Val Thr Ile Ser Cys Arg Ala Ser Gln Asp
        35                  40                  45

Ile Ser Asn Tyr Leu Asn Trp Tyr Gln Gln Lys Pro Asp Gly Thr Val
50                  55                  60

Lys Leu Leu Ile Tyr Tyr Thr Ser Arg Leu His Ser Gly Val Pro Ser
65                  70                  75                  80

Arg Phe Ser Gly Ser Gly Ser Gly Thr Asp Tyr Ser Leu Ser Ile Ser
                85                  90                  95

Asn Leu Glu Gln Glu Asp Ile Ala Thr Tyr Phe Cys Gln Gln Gly Asn
                100                 105                 110

Thr Phe Pro Leu Thr Phe Gly Ala Gly Thr Lys Leu Asp Leu Lys Arg
                115                 120                 125

Ala Asp Ala
    130

<210> SEQ ID NO 9
<211> LENGTH: 417
<212> TYPE: DNA
<213> ORGANISM: Artificial Sequence
<220> FEATURE:
<223> OTHER INFORMATION: heavy chain variable region coding sequence
<220> FEATURE:
<221> NAME/KEY: misc_feature
<222> LOCATION: (1)..(57)
<223> OTHER INFORMATION: Leader sequence
<220> FEATURE:
<221> NAME/KEY: misc_feature
<222> LOCATION: (58)..(132)
<223> OTHER INFORMATION: FR1
<220> FEATURE:
<221> NAME/KEY: misc_feature
<222> LOCATION: (133)..(162)
<223> OTHER INFORMATION: heavy chain CDR1
<220> FEATURE:
<221> NAME/KEY: misc_feature
<222> LOCATION: (163)..(204)
<223> OTHER INFORMATION: FR2
<220> FEATURE:
<221> NAME/KEY: misc_feature
<222> LOCATION: (205)..(255)
<223> OTHER INFORMATION: heavy chain CDR2
<220> FEATURE:
<221> NAME/KEY: misc_feature
<222> LOCATION: (256)..(351)
<223> OTHER INFORMATION: FR3
<220> FEATURE:
<221> NAME/KEY: misc_feature
<222> LOCATION: (352)..(384)
<223> OTHER INFORMATION: heavy chain CDR3
<220> FEATURE:
<221> NAME/KEY: misc_feature
<222> LOCATION: (385)..(417)
<223> OTHER INFORMATION: FR4

<400> SEQUENCE: 9
atggaatgga gctgggtttt tctctttctc ctgtcagtaa ctgcaggtgt tcactcccag    60
gtccagctgc agcagtctgg agctgagctg gtaaggcctg ggacttcagt gaaggtgtcc   120
tgcaaggctt ctggatacgc cttcactatt tacttgatag agtgggtaaa gcagaggcct   180
ggacagggcc ttgagtggat tggagtgatt aatcctggaa gtggtggtac taactacaat   240
gagaagttca agggcaaggc aacactgact gcagacaaat cctccagcac tgccttcatg   300

```
cagctcagca gcctgacatc tgatgactct gcggtttatt tctgtgcaag atcttattac    360
tacggttcct ttgctatgga ctactggggt caaggaacct cagtcaccgt ctctcag      417
```

<210> SEQ ID NO 10
<211> LENGTH: 139
<212> TYPE: PRT
<213> ORGANISM: Artificial Sequence
<220> FEATURE:
<223> OTHER INFORMATION: heavy chain variable region coding sequence
<220> FEATURE:
<221> NAME/KEY: misc_feature
<222> LOCATION: (1)..(19)
<223> OTHER INFORMATION: Leader sequence
<220> FEATURE:
<221> NAME/KEY: misc_feature
<222> LOCATION: (20)..(44)
<223> OTHER INFORMATION: FR1
<220> FEATURE:
<221> NAME/KEY: misc_feature
<222> LOCATION: (45)..(54)
<223> OTHER INFORMATION: heavy chain CDR1
<220> FEATURE:
<221> NAME/KEY: misc_feature
<222> LOCATION: (55)..(68)
<223> OTHER INFORMATION: FR2
<220> FEATURE:
<221> NAME/KEY: misc_feature
<222> LOCATION: (69)..(85)
<223> OTHER INFORMATION: heavy chain CDR2
<220> FEATURE:
<221> NAME/KEY: misc_feature
<222> LOCATION: (86)..(117)
<223> OTHER INFORMATION: FR3
<220> FEATURE:
<221> NAME/KEY: misc_feature
<222> LOCATION: (118)..(128)
<223> OTHER INFORMATION: heavy chain CDR3
<220> FEATURE:
<221> NAME/KEY: misc_feature
<222> LOCATION: (129)..(139)
<223> OTHER INFORMATION: FR4

<400> SEQUENCE: 10

```
Met Glu Trp Ser Trp Val Phe Leu Phe Leu Leu Ser Val Thr Ala Gly
1               5                   10                  15

Val His Ser Gln Val Gln Leu Gln Gln Ser Gly Ala Glu Leu Val Arg
            20                  25                  30

Pro Gly Thr Ser Val Lys Val Ser Cys Lys Ala Ser Gly Tyr Ala Phe
        35                  40                  45

Thr Ile Tyr Leu Ile Glu Trp Val Lys Gln Arg Pro Gly Gln Gly Leu
    50                  55                  60

Glu Trp Ile Gly Val Ile Asn Pro Gly Ser Gly Gly Thr Asn Tyr Asn
65                  70                  75                  80

Glu Lys Phe Lys Gly Lys Ala Thr Leu Thr Ala Asp Lys Ser Ser Ser
                85                  90                  95

Thr Ala Phe Met Gln Leu Ser Ser Leu Thr Ser Asp Asp Ser Ala Val
            100                 105                 110

Tyr Phe Cys Ala Arg Ser Tyr Tyr Gly Ser Phe Ala Met Asp Tyr
        115                 120                 125

Trp Gly Gln Gly Thr Ser Val Thr Val Ser Gln
    130                 135
```

<210> SEQ ID NO 11
<211> LENGTH: 392
<212> TYPE: DNA
<213> ORGANISM: Artificial Sequence
<220> FEATURE:

```
<223> OTHER INFORMATION: light chain variable region coding sequence
<220> FEATURE:
<221> NAME/KEY: misc_feature
<222> LOCATION: (1)..(60)
<223> OTHER INFORMATION: Leader sequence
<220> FEATURE:
<221> NAME/KEY: misc_feature
<222> LOCATION: (61)..(129)
<223> OTHER INFORMATION: FR1
<220> FEATURE:
<221> NAME/KEY: misc_feature
<222> LOCATION: (130)..(162)
<223> OTHER INFORMATION: light chain CDR1
<220> FEATURE:
<221> NAME/KEY: misc_feature
<222> LOCATION: (163)..(207)
<223> OTHER INFORMATION: FR2
<220> FEATURE:
<221> NAME/KEY: misc_feature
<222> LOCATION: (208)..(228)
<223> OTHER INFORMATION: light chain CDR2
<220> FEATURE:
<221> NAME/KEY: misc_feature
<222> LOCATION: (229)..(324)
<223> OTHER INFORMATION: FR3
<220> FEATURE:
<221> NAME/KEY: misc_feature
<222> LOCATION: (349)..(392)
<223> OTHER INFORMATION: FR4

<400> SEQUENCE: 11
atggtgtcct cagctcagtt ccttggtctc ctgttgctct gttttcaagg taccagatgt      60
gatgtccaga tgacacagac tatatcctcc ctgtctgcct ctctgggaga cagagtcacc     120
atcagttgca gggcaagtca ggacattggc aattatttaa actggtatca gcagaaacca     180
gatggaactg ttaaactcct gatctactac acatcaagat tacactcagg agtcccatca     240
aggttcagtg gcagtgggtc tggaacagat tattctctca ccattagcaa cctggagcaa     300
gaagatattg ccacttactt ttgccaacag gtaatacgc ttcggacgtt cggtggaggc      360
accaagctgg aaatcaaacg ggctgaatgc tg                                   392

<210> SEQ ID NO 12
<211> LENGTH: 130
<212> TYPE: PRT
<213> ORGANISM: Artificial Sequence
<220> FEATURE:
<223> OTHER INFORMATION: light chain variable region coding sequence
<220> FEATURE:
<221> NAME/KEY: misc_feature
<222> LOCATION: (1)..(20)
<223> OTHER INFORMATION: Leader sequence
<220> FEATURE:
<221> NAME/KEY: misc_feature
<222> LOCATION: (21)..(43)
<223> OTHER INFORMATION: FR1
<220> FEATURE:
<221> NAME/KEY: misc_feature
<222> LOCATION: (44)..(54)
<223> OTHER INFORMATION: light chain CDR1
<220> FEATURE:
<221> NAME/KEY: misc_feature
<222> LOCATION: (55)..(69)
<223> OTHER INFORMATION: FR2
<220> FEATURE:
<221> NAME/KEY: misc_feature
<222> LOCATION: (70)..(76)
<223> OTHER INFORMATION: light chain CDR2
<220> FEATURE:
<221> NAME/KEY: misc_feature
<222> LOCATION: (77)..(108)
<223> OTHER INFORMATION: FR3
<220> FEATURE:
<221> NAME/KEY: misc_feature
```

```
<222> LOCATION: (109)..(116)
<223> OTHER INFORMATION: light chain CDR3
<220> FEATURE:
<221> NAME/KEY: misc_feature
<222> LOCATION: (117)..(130)
<223> OTHER INFORMATION: FR4

<400> SEQUENCE: 12

Met Val Ser Ser Ala Gln Phe Leu Gly Leu Leu Leu Cys Phe Gln
1               5                   10                  15

Gly Thr Arg Cys Asp Val Gln Met Thr Gln Thr Ile Ser Ser Leu Ser
            20                  25                  30

Ala Ser Leu Gly Asp Arg Val Thr Ile Ser Cys Arg Ala Ser Gln Asp
        35                  40                  45

Ile Gly Asn Tyr Leu Asn Trp Tyr Gln Gln Lys Pro Asp Gly Thr Val
    50                  55                  60

Lys Leu Leu Ile Tyr Tyr Thr Ser Arg Leu His Ser Gly Val Pro Ser
65                  70                  75                  80

Arg Phe Ser Gly Ser Gly Ser Gly Thr Asp Tyr Ser Leu Thr Ile Ser
                85                  90                  95

Asn Leu Glu Gln Glu Asp Ile Ala Thr Tyr Phe Cys Gln Gln Gly Asn
            100                 105                 110

Thr Leu Arg Thr Phe Gly Gly Gly Thr Lys Leu Glu Ile Lys Arg Ala
        115                 120                 125

Glu Cys
    130

<210> SEQ ID NO 13
<211> LENGTH: 10
<212> TYPE: PRT
<213> ORGANISM: Artificial Sequence
<220> FEATURE:
<223> OTHER INFORMATION: heavy chain CDR1

<400> SEQUENCE: 13

Gly Tyr Ile Phe Arg Asn Tyr Gly Met Asn
1               5                   10

<210> SEQ ID NO 14
<211> LENGTH: 17
<212> TYPE: PRT
<213> ORGANISM: Artificial Sequence
<220> FEATURE:
<223> OTHER INFORMATION: heavy chain CDR2

<400> SEQUENCE: 14

Trp Ile Asn Thr Tyr Thr Gly Glu Pro Thr Tyr Ala Asp Asp Phe Lys
1               5                   10                  15

Gly

<210> SEQ ID NO 15
<211> LENGTH: 12
<212> TYPE: PRT
<213> ORGANISM: Artificial Sequence
<220> FEATURE:
<223> OTHER INFORMATION: heavy chain CDR3

<400> SEQUENCE: 15

Arg Gly Trp Leu Leu Thr Gly Gly Ala Met Asp Tyr
1               5                   10

<210> SEQ ID NO 16
```

```
<211> LENGTH: 11
<212> TYPE: PRT
<213> ORGANISM: Artificial Sequence
<220> FEATURE:
<223> OTHER INFORMATION: light chain CDR1

<400> SEQUENCE: 16

Arg Ala Ser Gln Asp Ile Gly Ser Ser Leu Asn
1               5                   10

<210> SEQ ID NO 17
<211> LENGTH: 7
<212> TYPE: PRT
<213> ORGANISM: Artificial Sequence
<220> FEATURE:
<223> OTHER INFORMATION: light chain CDR2

<400> SEQUENCE: 17

Ala Thr Ser Ser Leu Asp Ser
1               5

<210> SEQ ID NO 18
<211> LENGTH: 9
<212> TYPE: PRT
<213> ORGANISM: Artificial Sequence
<220> FEATURE:
<223> OTHER INFORMATION: light chain CDR3

<400> SEQUENCE: 18

Leu Gln Tyr Val Ser Ser Pro Trp Thr
1               5

<210> SEQ ID NO 19
<211> LENGTH: 10
<212> TYPE: PRT
<213> ORGANISM: Artificial Sequence
<220> FEATURE:
<223> OTHER INFORMATION: heavy chain CDR1

<400> SEQUENCE: 19

Gly Tyr Ile Phe Arg Asn Tyr Gly Met Asn
1               5                   10

<210> SEQ ID NO 20
<211> LENGTH: 17
<212> TYPE: PRT
<213> ORGANISM: Artificial Sequence
<220> FEATURE:
<223> OTHER INFORMATION: heavy chain CDR2

<400> SEQUENCE: 20

Trp Ile Asn Thr Tyr Thr Gly Glu Pro Thr Tyr Ala Asp Asp Phe Lys
1               5                   10                  15

Gly

<210> SEQ ID NO 21
<211> LENGTH: 12
<212> TYPE: PRT
<213> ORGANISM: Artificial Sequence
<220> FEATURE:
<223> OTHER INFORMATION: heavy chain CDR3

<400> SEQUENCE: 21

Asp Cys Gly Thr Ser His Tyr Tyr Ala Met Asp Tyr
1               5                   10
```

```
<210> SEQ ID NO 22
<211> LENGTH: 11
<212> TYPE: PRT
<213> ORGANISM: Artificial Sequence
<220> FEATURE:
<223> OTHER INFORMATION: light chain CDR1

<400> SEQUENCE: 22

Arg Ala Ser Gln Asp Ile Ser Asn Tyr Leu Asn
1               5                   10

<210> SEQ ID NO 23
<211> LENGTH: 7
<212> TYPE: PRT
<213> ORGANISM: Artificial Sequence
<220> FEATURE:
<223> OTHER INFORMATION: light chain CDR2

<400> SEQUENCE: 23

Tyr Thr Ser Arg Leu His Ser
1               5

<210> SEQ ID NO 24
<211> LENGTH: 9
<212> TYPE: PRT
<213> ORGANISM: Artificial Sequence
<220> FEATURE:
<223> OTHER INFORMATION: light chain CDR3

<400> SEQUENCE: 24

Gln Gln Gly Asn Thr Phe Pro Leu Thr
1               5

<210> SEQ ID NO 25
<211> LENGTH: 10
<212> TYPE: PRT
<213> ORGANISM: Artificial Sequence
<220> FEATURE:
<223> OTHER INFORMATION: heavy chain CDR1

<400> SEQUENCE: 25

Gly Tyr Ala Phe Thr Ile Tyr Leu Ile Glu
1               5                   10

<210> SEQ ID NO 26
<211> LENGTH: 17
<212> TYPE: PRT
<213> ORGANISM: Artificial Sequence
<220> FEATURE:
<223> OTHER INFORMATION: heavy chain CDR2

<400> SEQUENCE: 26

Val Ile Asn Pro Gly Ser Gly Gly Thr Asn Tyr Asn Glu Lys Phe Lys
1               5                   10                  15

Gly

<210> SEQ ID NO 27
<211> LENGTH: 11
<212> TYPE: PRT
<213> ORGANISM: Artificial Sequence
<220> FEATURE:
<223> OTHER INFORMATION: heavy chain CDR3

<400> SEQUENCE: 27

Ser Tyr Tyr Tyr Gly Ser Phe Ala Met Asp Tyr
1               5                   10
```

```
<210> SEQ ID NO 28
<211> LENGTH: 11
<212> TYPE: PRT
<213> ORGANISM: Artificial Sequence
<220> FEATURE:
<223> OTHER INFORMATION: light chain CDR1

<400> SEQUENCE: 28

Arg Ala Ser Gln Asp Ile Gly Asn Tyr Leu Asn
1               5                   10

<210> SEQ ID NO 29
<211> LENGTH: 7
<212> TYPE: PRT
<213> ORGANISM: Artificial Sequence
<220> FEATURE:
<223> OTHER INFORMATION: light chain CDR2

<400> SEQUENCE: 29

Tyr Thr Ser Arg Leu His Ser
1               5

<210> SEQ ID NO 30
<211> LENGTH: 8
<212> TYPE: PRT
<213> ORGANISM: Artificial Sequence
<220> FEATURE:
<223> OTHER INFORMATION: light chain CDR3

<400> SEQUENCE: 30

Gln Gln Gly Asn Thr Leu Arg Thr
1               5
```